United States Patent
Sengupta et al.

(10) Patent No.: US 9,269,731 B2
(45) Date of Patent: Feb. 23, 2016

(54) INTEGRATED TERAHERTZ IMAGING SYSTEMS

(71) Applicant: California Institute of Technology, Pasadena, CA (US)

(72) Inventors: Kaushik Sengupta, Pasadena, CA (US); Seyed Ali Hajimiri, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 14/150,670

(22) Filed: Jan. 8, 2014

(65) Prior Publication Data
US 2014/0367575 A1 Dec. 18, 2014

Related U.S. Application Data

(63) Continuation of application No. 13/693,025, filed on Dec. 3, 2012, now Pat. No. 8,658,976.

(60) Provisional application No. 61/565,770, filed on Dec. 1, 2011.

(51) Int. Cl.
| H01L 27/146 | (2006.01) |
| G01N 21/3581 | (2014.01) |
| G01J 5/08 | (2006.01) |

(52) U.S. Cl.
CPC .......... *H01L 27/14609* (2013.01); *G01J 5/0837* (2013.01); *G01N 21/3581* (2013.01); *H01L 27/14649* (2013.01); *H01L 27/14601* (2013.01)

(58) Field of Classification Search
CPC .............. G01J 5/0837; G01N 21/3581; H01L 27/14601; H01L 27/14609; H01L 27/14649
See application file for complete search history.

(56) References Cited

U.S. PATENT DOCUMENTS

| 6,218,998 B1 | 4/2001 | Van Voorhies |
| 6,600,451 B2 | 7/2003 | Mimura et al. |
| 7,573,432 B1 | 8/2009 | Eydelman et al. |
| 7,952,061 B2 | 5/2011 | Hillis et al. |
| 2002/0105470 A1 | 8/2002 | Kim |
| 2004/0065831 A1 | 4/2004 | Federici et al. |
| 2005/0179606 A1 | 8/2005 | Holly |
| 2006/0076493 A1 | 4/2006 | Bluzer |
| 2006/0111619 A1 | 5/2006 | Castiglione et al. |

(Continued)

FOREIGN PATENT DOCUMENTS

| JP | 2010-200207 A | 9/2010 |
| KR | 10-0692420 B1 | 3/2007 |

(Continued)

OTHER PUBLICATIONS

International Preliminary Report on Patentability for PCT Application No. PCT/US2012/067649 mailed Jun. 12, 2014, 6 pages.

(Continued)

*Primary Examiner* — Mark R Gaworecki
(74) *Attorney, Agent, or Firm* — Ardeshir Tabibi, Esq.; Alston & Bird LLP

(57) ABSTRACT

A low-power 4×4-pixel THz camera with responsivity greater than 2.5 MV/W and sub-10 pW/√Hz NEP at 0.25 THz is integrated in 130 nm silicon without using either high-resistivity substrates or silicon lenses. Imaging results with a fully integrated radiating CMOS power source demonstrate the first entirely silicon-based THz imager.

11 Claims, 29 Drawing Sheets

(56) References Cited

U.S. PATENT DOCUMENTS

| | | | |
|---|---|---|---|
| 2006/0210279 A1* | 9/2006 | Hillis et al. | 398/118 |
| 2006/0239688 A1* | 10/2006 | Hillis et al. | 398/116 |
| 2007/0235658 A1 | 10/2007 | Zimdars et al. | |
| 2011/0254727 A1* | 10/2011 | Kam et al. | 342/179 |
| 2011/0315880 A1 | 12/2011 | Nemirovsky | |
| 2013/0082181 A1 | 4/2013 | Corcos et al. | |
| 2013/0082345 A1 | 4/2013 | Corcos et al. | |
| 2013/0193324 A1 | 8/2013 | Sengupta et al. | |

FOREIGN PATENT DOCUMENTS

| | | |
|---|---|---|
| WO | 2012/094051 A3 | 7/2012 |
| WO | 2013/082622 A2 | 6/2013 |

OTHER PUBLICATIONS

International Search Report for PCT Application No. PCT/US2012/067649 mailed May 30, 2013.

International Search Report and Written Opinion for PCT Application No. PCT/US2011/057899 mailed Aug. 3, 2012.

International Preliminary Report on Patentability for PCT Application No. PCT/US2011/057899 mailed Apr. 30, 2013.

Notice of Allowance for U.S. Appl. No. 13/693,025 mailed Jun. 28, 2013.

Notice of Allowance for U.S. Appl. No. 13/693,025 mailed Oct. 9, 2013.

* cited by examiner

ALL PRIOR ART

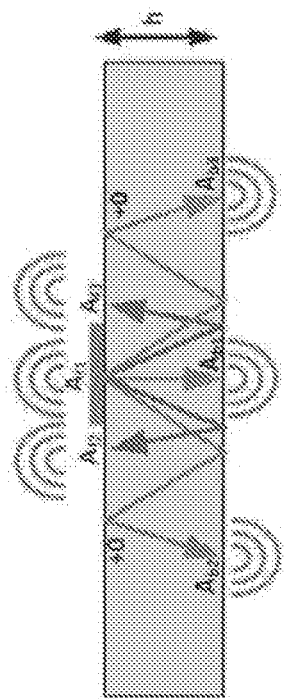
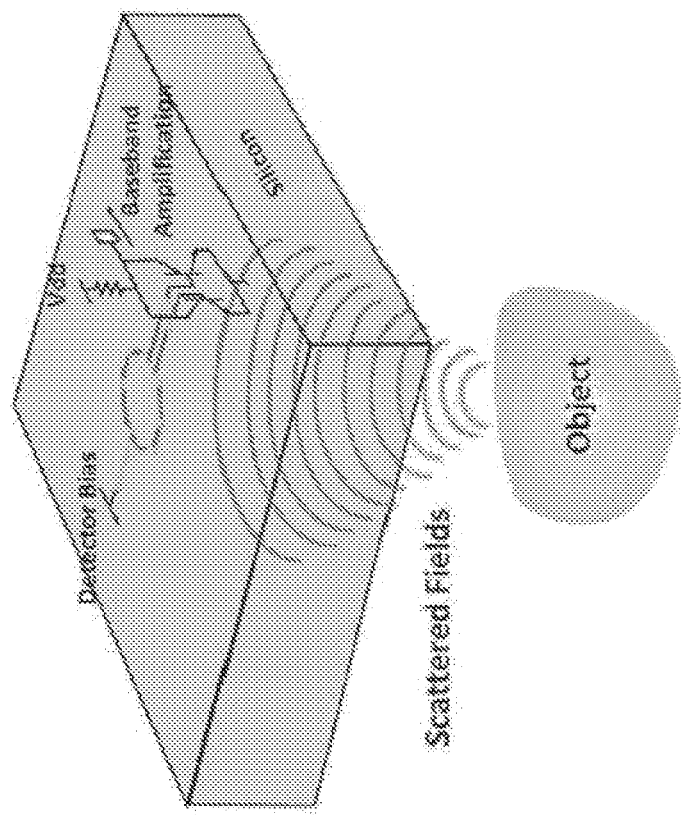
FIG. 4B
FIG. 4A

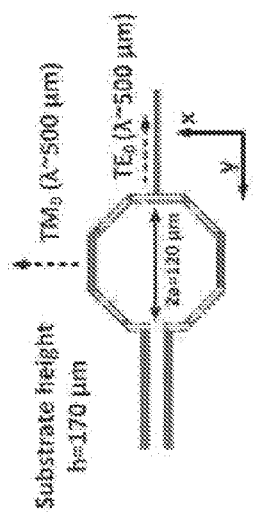
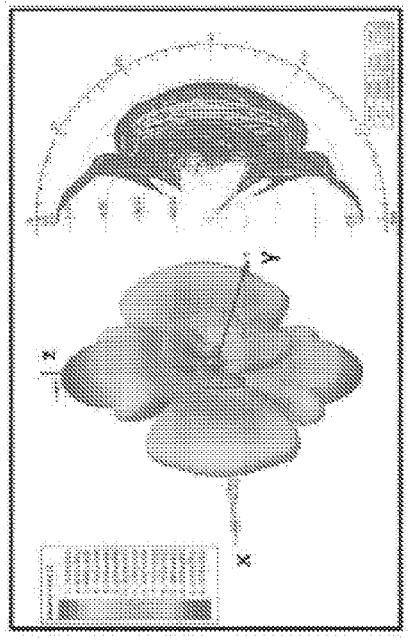
FIG. 6A
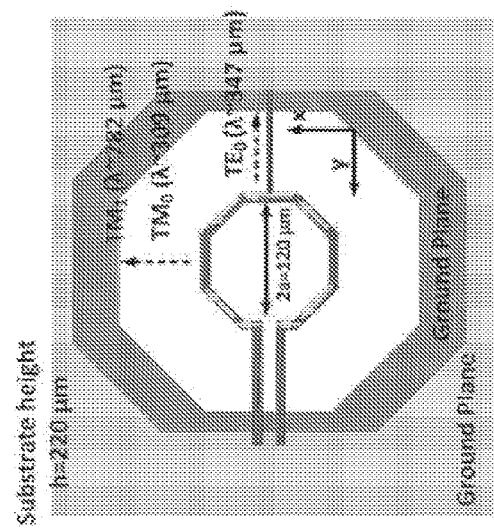
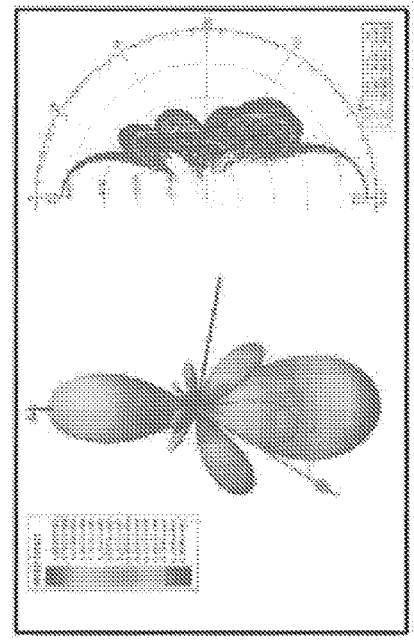
FIG. 6C
FIG. 6D

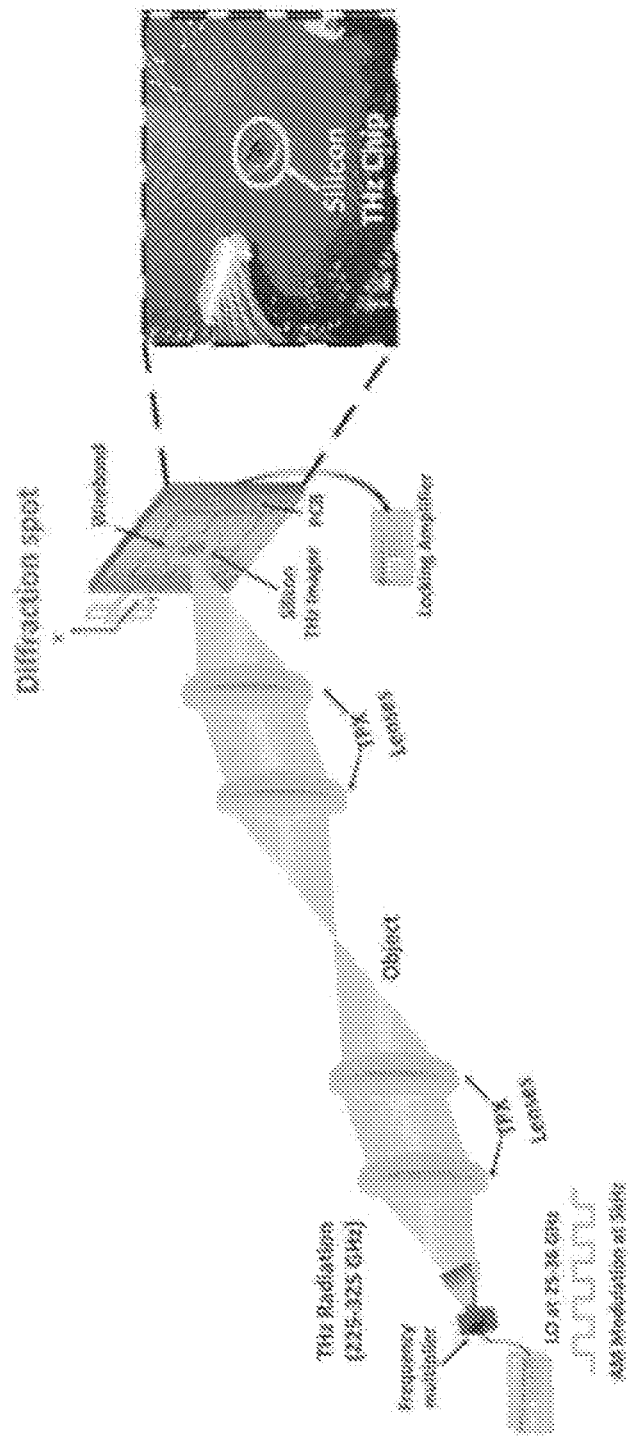

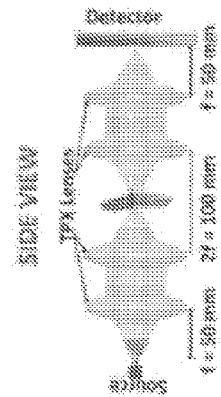
FIG. 16E
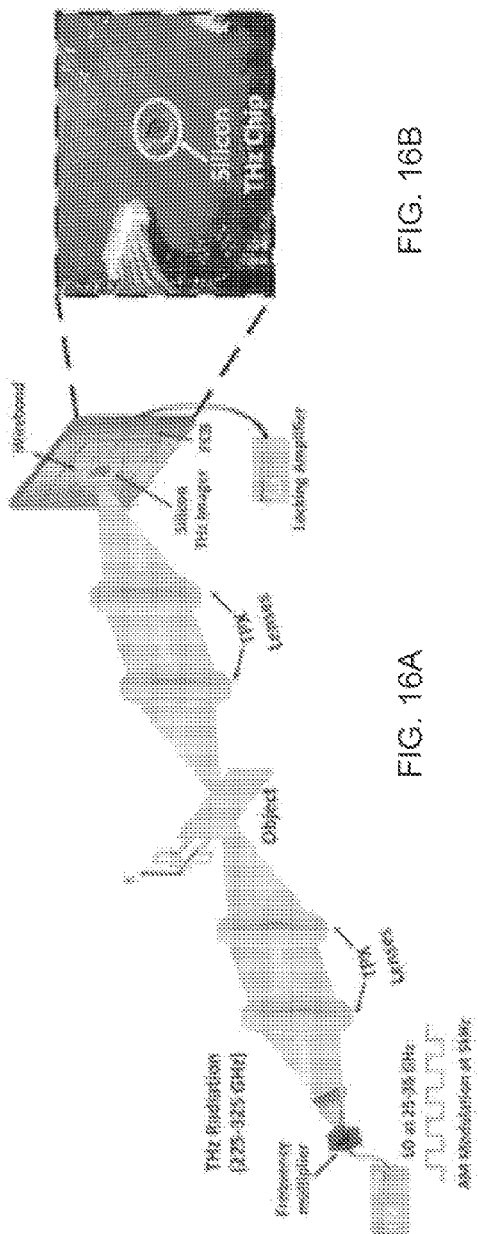
FIG. 16B
FIG. 16A
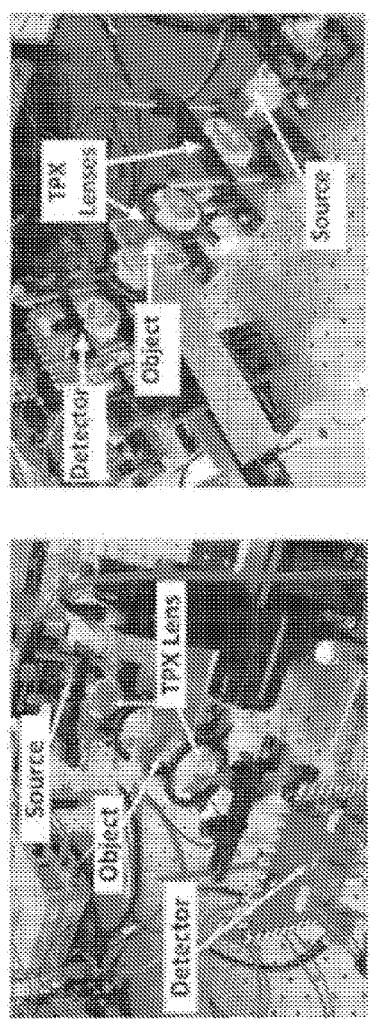
FIG. 16D
FIG. 16C

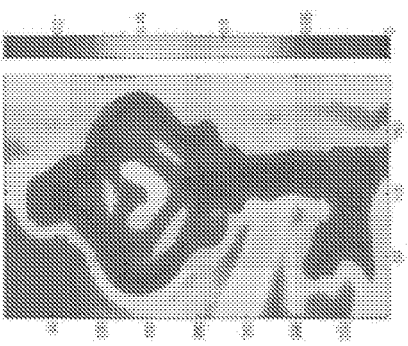
FIG. 18B
FIG. 18A
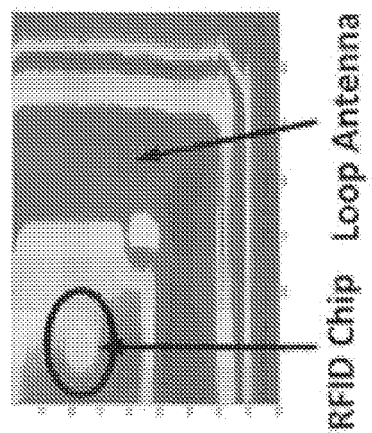
FIG. 18D
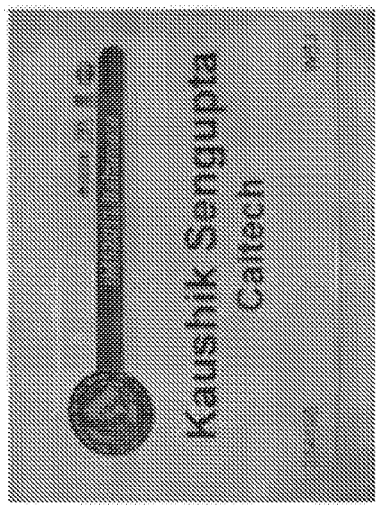
FIG. 18C

FIG. 19A
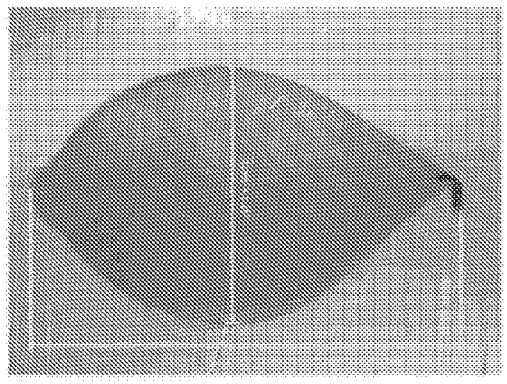
FIG. 19B
FIG. 19C
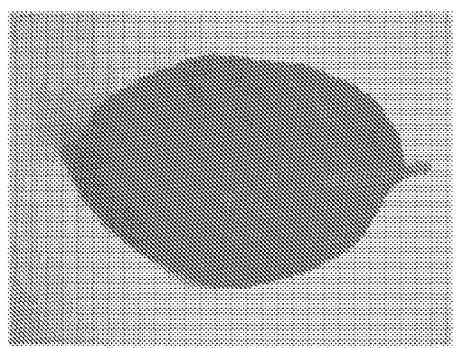
FIG. 19D
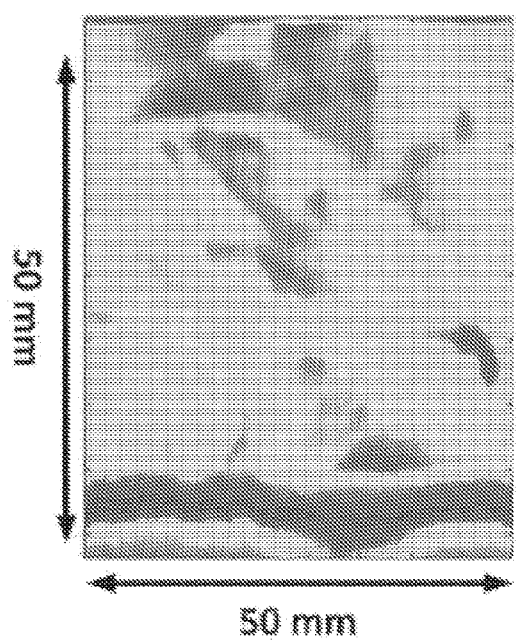
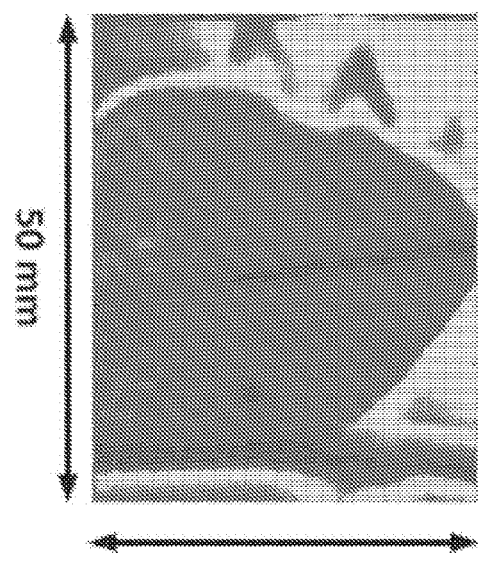

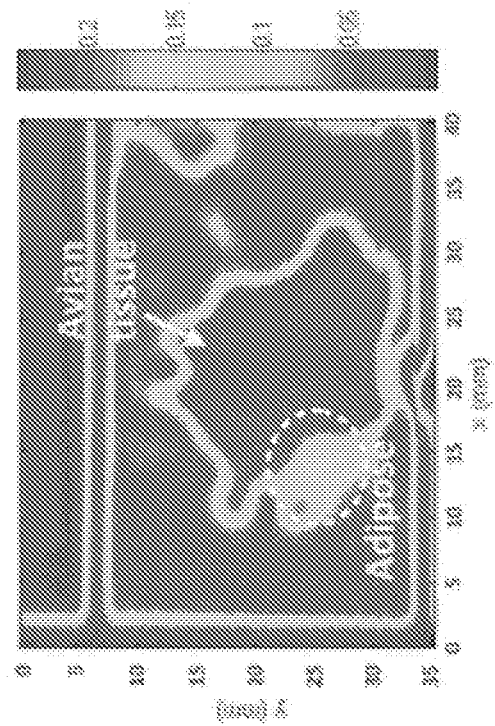
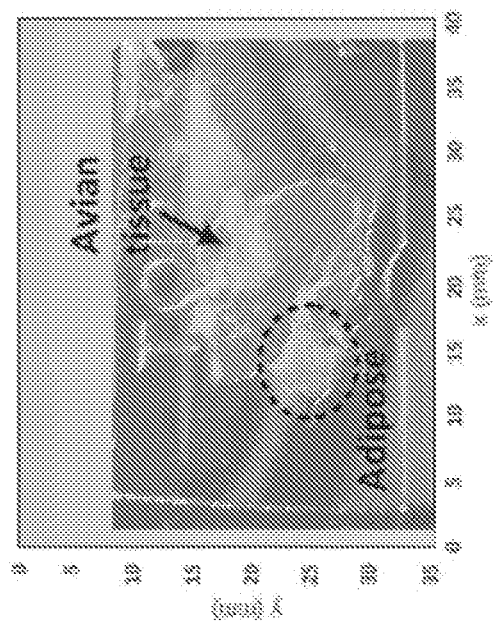
FIG. 20A
FIG. 20B

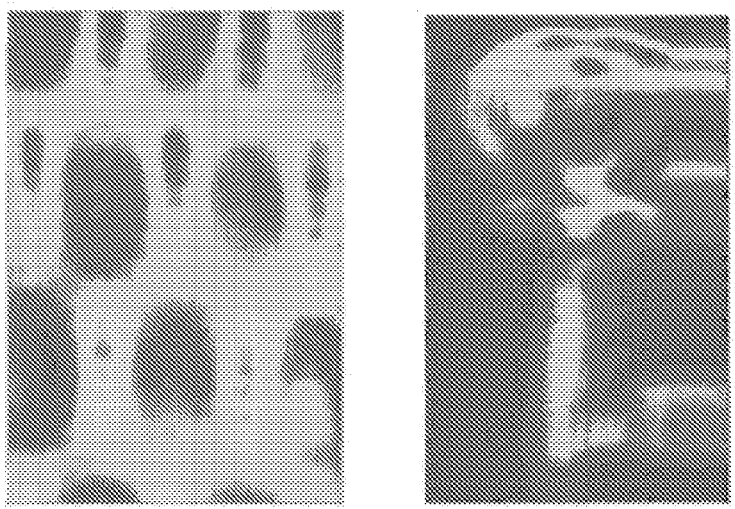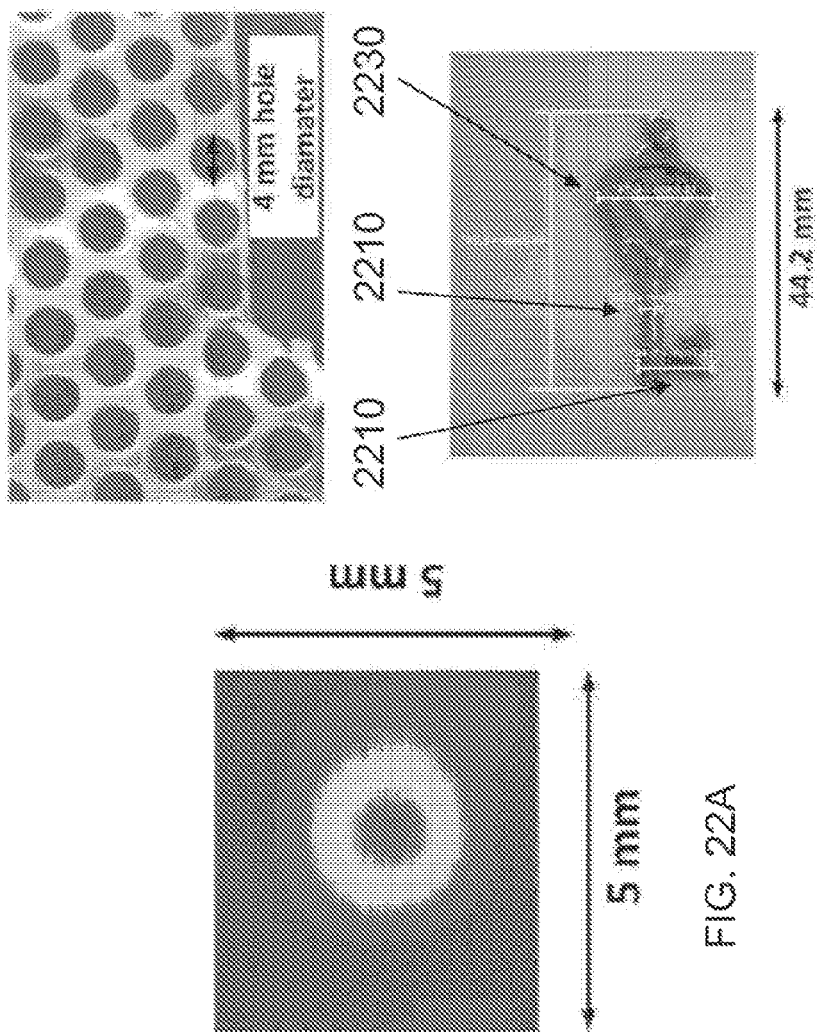
FIG. 22C
FIG. 22E
FIG. 22B
FIG. 22D
FIG. 22A

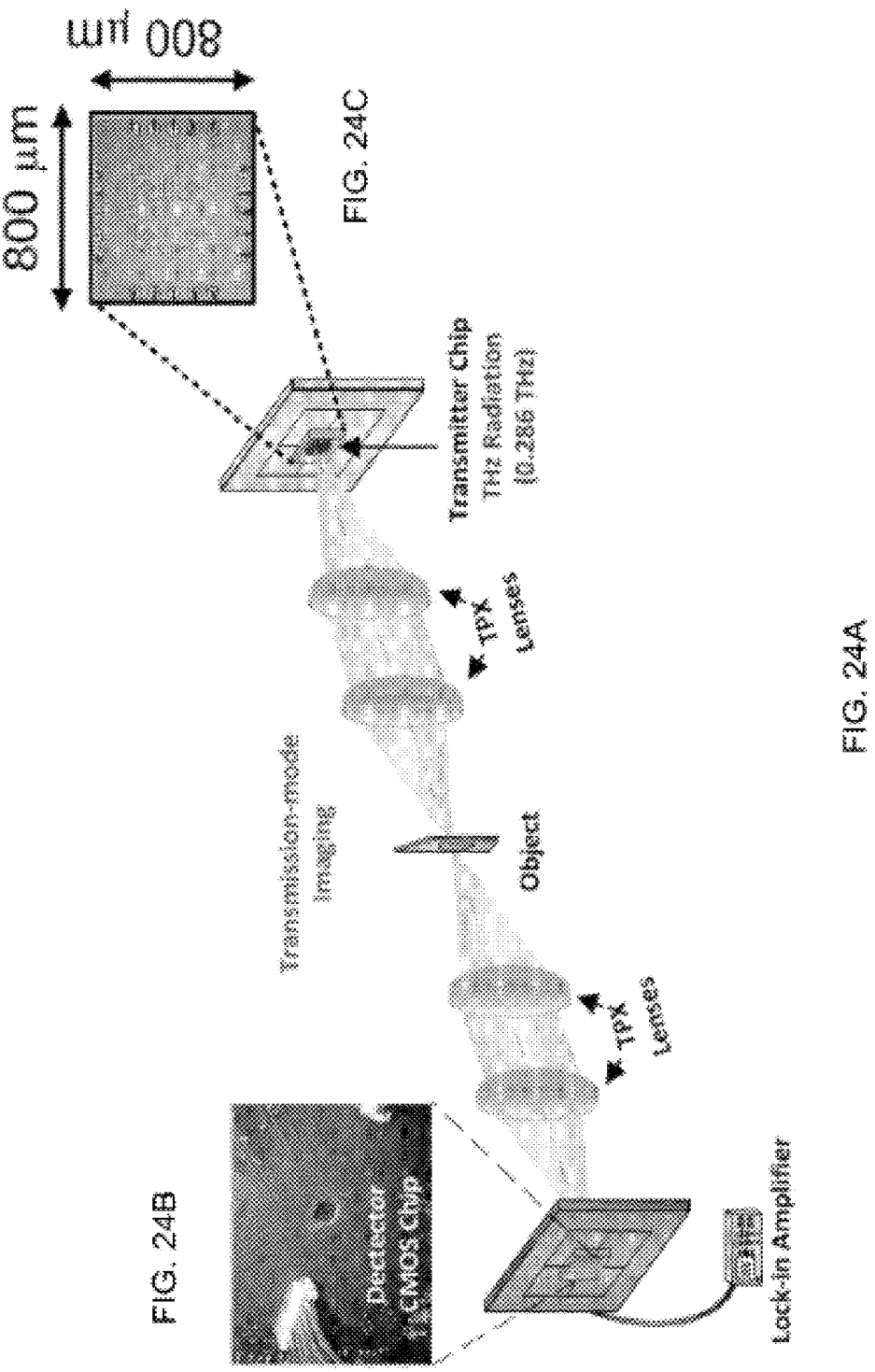

INTEGRATED TERAHERTZ IMAGING SYSTEMS

CROSS-REFERENCE TO RELATED APPLICATIONS

This application claims priority to and is a continuation of U.S. application Ser. No. 13/693,025, filed on Dec. 3, 2012, entitled "INTEGRATED TERAHERTZ IMAGING SYSTEMS", which application claims the benefit of priority to U.S. Provisional Application Ser. No. 61/565,770, filed on Dec. 1, 2011, entitled "INTEGRATED TERAHERTZ IMAGING SYSTEMS IN SILICON", the contents of which are incorporated herein by reference in their entirety.

STATEMENT REGARDING FEDERALLY FUNDED RESEARCH OR DEVELOPMENT

This invention was made with government support under FA8650-09-C-7924 awarded by the Air Force. The government has certain rights in the invention.

FIELD OF THE INVENTION

The invention relates to imaging systems in general and particularly to Terahertz imaging systems.

BACKGROUND OF THE INVENTION

For many years terahertz receivers and imagers have been, used in fields of study is astronomy and chemical sciences for high-resolution spectroscopy and remote sensing areas. In recent years, them has been significant research devoted to Terahertz technology. Because of some of its unique properties it is emerging as an attractive tool for a wider range of applications such as security screening (due to its ability to penetrate through clothing, plastic and packaging materials with higher resolution than microwaves and mm-waves) (See for example, P. H. Siegel, "Terahertz technology," *IEEE Trans. Microw. Theory Tech.*, vol. 50, no. 3, pp. 910-928, 2002), noninvasive medical imaging (lower scattering compared to optics, contrast in water absorption and tissue density and safe due its nonionizing photon energies) (see, for example, P. H. Siegel, "Terahertz technology in biology and medicine," *IEEE Trans. Microw. Theory Tech.*, vol. 52, no. 10, pp. 2438-2447, 2004; J-H Son, "Terahertz electromagnetic interactions with biological matter and their applications," *J. Appl. Phys.* 105, 102033, 2009), spectroscopic studies and label-free biosensing (see for example, P. H. Bolivar, et al., "Label-free probing of genes by time domain terahertz sensing," *Phys. Med. Biol.*, vol. 47, no. 21, pp. 3815-3821, November 2002), contraband detection (See, for example, R. Appleby and H. B. Wallace, "Standoff Detection of Weapons and Contraband in the 100 GHz to 1 THz Region," *IEEE Trans. Antennas Propag.*, vol. 55, no. 11, pp. 2944-2955, November 2007), and industrial and process control. Current THz detector technology comprise discrete and custom devices, which are often bulky and expensive, while not sensitive enough at room temperature. They can be optics-based (such as nonlinear crystals or electro-optic samplers), calorimetric detector technologies (such as bolometers, Golay cells, pyroelectric detectors which are limited by thermal-time constants for their use in video-rate imaging), or solid-state hybrid III-V MMICs (which have higher cost and are less amenable to integration).

FIG. 1A through FIG. 1D illustrate some typical THz detector technology currently in use for astronomical sciences. Comprehensive articles on this subject include P. H. Siegel and R. J. Dengler, "Terahertz heterodyne imaging part I: Introduction and Techniques," *Intl. Jour. Infrared Millimeter Waves.*, vol. 27, no. 4, pp. 465-477, April 2006; and P. H. Siegel and R. J. Dengler, "Terahertz heterodyne imaging part II: Instruments," *Intl. Jour. Infrared Millimeter Waves.*, vol. 27, no. 5, pp. 631-655, May, 2006. The important figure of merits for a detector are Responsivity (Rv) and Noise-equivalent-power (NEP). Responsivity is defined as the change in output DC voltage with a unit change in input RF power. NEP is defined as the input power for which the signal-to-noise ratio is unity for an integration time of 1 second.

Prior work and contemporary work have demonstrated the feasibility of silicon technology for THz detection. See, for example, Erik Ojefors et al., "A 820 GHz SiGe Chipset for Terahertz Active Imaging Applications," *ISSCC Dig. Tech. Paper, pp.* 224-225, February 2011; E. Ojefors, U. R. Pfeiffer, "A 650 GHz SiGe Receiver Front-End for Terahertz Imaging Arrays", *ISSCC Dig. Tech. Papers, pp.* 430-431, February 2010; H. Sherry et al., "Lens-Integrated THz Imaging Arrays in 65 nm CMOS Technologies," *RFIC Symp. Dig.*, pp. 1-4, June 2011; and F. Schuster et al., "A Broadband THz Imager in a Low-Cost CMOS Technology," *ISSCC Dig. Tech. Papers, pp.* 42-43, February 2011. However they can be power-intensive (>300 mW/pixel), require high-resistivity substrates (>1 KΩ-cm) substrates, or use modifications such as silicon lenses or substrate thinning. The main reason necessitating the use of these modifications is the low efficiency of on-chip receiving antennas.

There is a need for improved Terahertz imagers and imaging systems.

SUMMARY OF THE INVENTION

According to one aspect, the invention features a Terahertz camera. The Terahertz camera comprises an integrated imager chip having a plurality of pixels fabricated therein, the imager chip configured to respond, to incoming Terahertz radiation and configured to provide an electronic signal representative of an intensity of the incoming Terahertz radiation at each of the plurality of pixels, each pixel of the plurality of pixels of the integrated imager chip comprising an onchip antenna configured to detect the incoming Terahertz radiation, each, pixel of the plurality of pixels of the integrated imager chip comprising, a front-end receiver circuit configured to reduce a Terahertz frequency of the incoming Terahertz radiation to a frequency amenable to processing in circuitry on the integrated imager chip; and the integrated imager chip having a plurality of output terminals, each of the plurality of output terminals configured to provide as output signal for a respective one of the plurality of pixels.

In one embodiment, each pixel of the plurality of pixels of the integrated imager chip comprises a low-frequency amplifier.

In another embodiment, the low-frequency amplifier has a controllable gain.

In yet another embodiment, the low-frequency amplifier has a controllable frequency response.

In still another embodiment, the front-end receiver circuit of at least one pixel of the plurality of pixels is configured to convert the incoming Terahertz radiation into a change in output DC voltage.

In a further embodiment, the front-end receiver circuit of at least one pixel of the plurality of pixels is configured to convert the incoming Terahertz radiation to an intermediate frequency through harmonic mixing.

In yet a further embodiment, at least one pixel of the plurality of pixels further comprises a an onchip full-wavelength loop antenna.

In an additional embodiment, the Terahertz camera further comprises an onchip metal plane having an aperture defined therein in registry with the onchip full-wavelength loop antenna.

In one more embodiment, a dimension of the aperture defined in the moral plane is configured to maximize the responsivity of the Terahertz camera.

In still a further embodiment, the integrated imager chip is realized on a substrate that has a thickness that is controlled.

In one embodiment, the integrated imager chip is configured to receive radiation from one of a backside and a frontside of a substrate.

In another embodiment, the integrated imager chip is mounted on a metal plane to receive radiation from the frontside of the substrate.

In still another embodiment, the integrated imager chip is fabricated in silicon.

In a further embodiment, the integrated imager chip is fabricated in a compound semiconductor.

According to another aspect, the invention relates to an integrated Terahertz imaging apparatus that includes a Terahertz camera that comprises an integrated imager chip having a plurality of pixels fabricated therein, the imager chip configured to respond to incoming Terahertz radiation and configured to provide an electronic signal representative of an intensity of the incoming Terahertz radiation at each of the plurality of pixels, each pixel of the plurality of pixels of the integrated imager chip comprising an onchip antenna configured to detect the incoming Terahertz radiation, each pixel of the plurality of pixels of the integrated imager chip comprising a front-end receiver circuit configured to reduce a Terahertz frequency of the incoming Terahertz radiation to a frequency amenable to processing in circuitry on the integrated imager chip; and the integrated imager chip having a plurality of output terminals, each of the plurality of output terminals configured to provide an output signal for a respective one of the plurality of pixels; and a source of Terahertz radiation configured to provide Terahertz radiation to which the Terahertz camera is configured to be responsive.

In still another embodiment, the integrated imager chip is fabricated in a semiconductor material selected from the group of materials consisting of silicon and a compound semiconductor.

In one embodiment, the integrated Terahertz imaging apparatus is configured to operate is a transmission geometry.

In another embodiment, the integrated Terahertz imaging apparatus is configured to operate in a reflection geometry.

In yet another embodiment, the integrated Terahertz imaging apparatus is configured to provide an image is the form of a Fourier transform.

In still another embodiment, the integrated Terahertz imaging apparatus is configured to receive an image cast directly on a focal plane of a lens.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 4A is a perspective diagram of a full-wavelength loop antenna on an ungrounded substrate.

FIG. 4B is a schematic cross-sectional diagram of an oscillating current element on an ungrounded substrate.

FIG. 6A is a schematic diagram of a full-wavelength loop antenna without a ground plane and without an aperture opening.

FIG. 6B is a diagram that illustrates the three dimensional form of the radiated signal and also shows the 2D radiation profile of the antenna of FIG. 6A.

FIG. 6C is a schematic diagram of a full-wavelength loop antenna with a ground plane and with an aperture opening.

FIG. 6D is a diagram, that illustrates the three dimensional form of the radiated signal and also shows the 2D radiation profile of the antenna of FIG. 6C.

FIG. 13A is a diagram showing a measurement setup for focusing emitted THz beam to a diffraction-limited spot size on the focal plane which is imaged by the THz receiver by raster-scanning.

FIG. 13B is an image of the silicon THz imager mounted on a PCB.

FIG. 16A is a diagram showing a measurement setup for making transmission-mode images in perspective view.

FIG. 16B is an image of the silicon THz imager mounted on a PCB.

FIG. 16C and FIG. 16D are images of parts of the measurement setup for making transmission mode images.

FIG. 16E is a diagram showing a measurement setup for making transmission-mode images in side view.

FIG. 18A is an optical image and FIG. 18B is a THz transmission line image of a key.

FIG. 18C is an optical image of a conference ID badge, and FIG. 18D is a THz transmission line image of the RFID chip and the loop antenna inside the conference ID badge.

FIG. 19A is an optical image and FIG. 19B is a THz transmission image of a dry (dessicated) leaf.

FIG. 19C is an optical image and FIG. 19D is a THz transmission image of a green (water-containing) leaf.

FIG. 20A is an optical image and FIG. 20B is a transmission image of chicken tissue.

FIG. 22A is an image showing the measured spot size of the focused beam at 0.26 THz on the focal plane in reflection-mode setup.

FIG. 22B is an optical image of a metal screen having holes of 4 mm, diameter and FIG. 22C is a reflection mode THz image of the screen.

FIG. 22D is an optical image of a metal key and FIG. 22E is a reflection mode THz image of the screen.

FIG. 24A is a perspective schematic diagram of an all-silicon THz imaging setup with a 16-pixel BiCMOS detector array and 2×2 array of locked CMOS DARs near 0.29 THz.

FIG. 24B is an image of the detector mounted on a PCB.

FIG. 24C is an image of the 2×2 array transmitter chip, which measures 800 μm on a side.

DETAILED DESCRIPTION

The Terahertz frequency range is generally taken as the frequency spectrum between 0.3-3 THz. Unless otherwise specified, in the present discussion the term "THz" is used to refer even to frequencies above 0.1 THz and near 0.3 THz, but the invention is amenable to applications over and beyond the entire Terahertz frequency range. THz is synonymously referred to as the sub-millimeter wave band, or as the wavelength ranges from 1 mm to 100 μm, which corresponds to photon energies between 1.2-12.4 meV and is equivalent to radiation from a blackbody having a temperature in the range of 14-140 K.

Figures 1A, 1B, 1C, 1D:
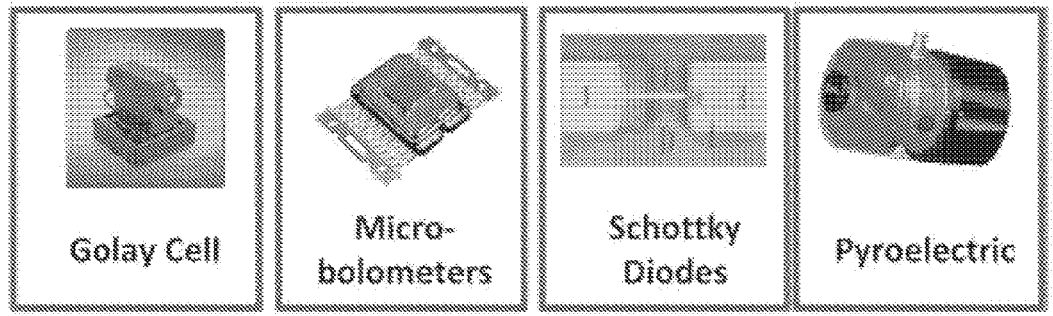
FIG. 1A through FIG. 1D are illustrations of some of the typical and currently used prior art Terahertz direct detection technologies. Golay Cells have a typical NEP of approximately 200 pW/√Hz, microbolometers have a typical NEP of approximately 10-200 pW/√Hz, Schottky Barrier Diodes have a typical NEP of approximately 10-20 pW/√Hz, and pyroelectric detectors have a typical NEP of approximately 400 pW/√Hz.
Figure 2:
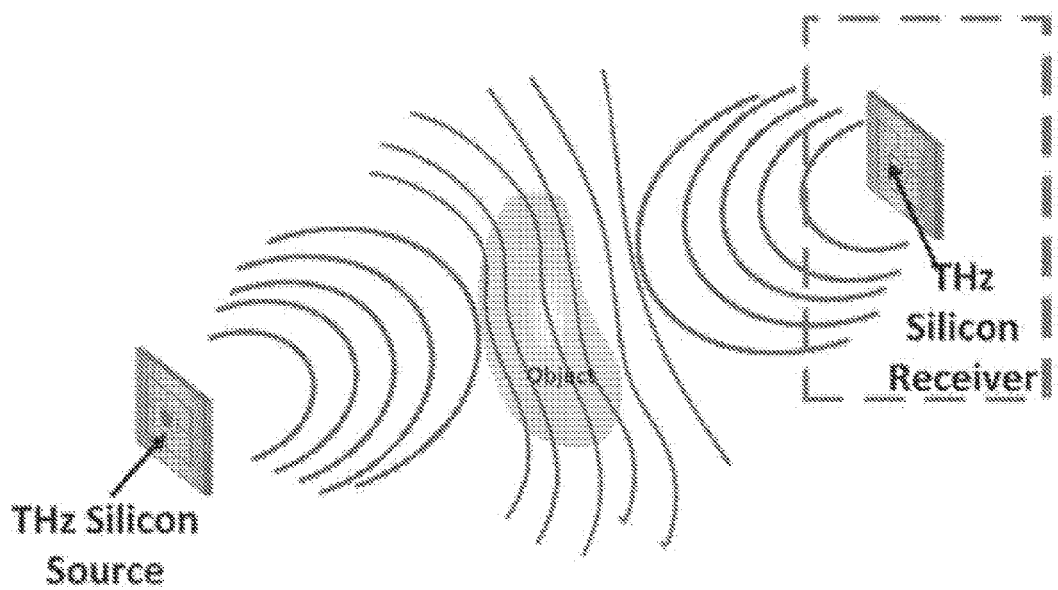
FIG. 2 is a schematic diagram of a silicon-based Terahertz imaging system.

Integrated terahertz sources, radiators and beam-scanners in integrated silicon technology have been described in U.S. Ser. No. 13/282,192, in order to enable the realization, of an all-silicon THz imager, we now describe the receiver portion, of a transceiver system as shown in FIG. 2. FIG. 2 is a schematic diagram of a silicon-based Terahertz imaging system.

While the present invention is described as being fabricated in silicon, it is understood that equivalent imaging systems can be fabricated using many different types of semiconductor devices such as MOSFETs, JFETs, HEMTs, HBTs and others which can be realized using silicon or using III-V compound semiconductor fabrication processes that employ GaAs, InP, GaN, InGaAs, and similar compound semiconductor material systems.

The important figure of merits for a detector are Responsivity ($\mathcal{R}_v$) and Noise-equivalent-power (NEP). Responsivity is defined as the change in output DC voltage with a unit change in input RF power. NEP is defined as the input power for which the signal-to-noise ratio is unity for an integration time of 1 second. If $v_n$ is the output rms noise voltage, and $\mathcal{R}_v$ is the Responsivity, NEP is defined as $$NEP = \frac{v_n}{\mathcal{R}_v}$$

Typical NEP achieved in prior art devices at room temperature have been described hereinabove. It is expected that if silicon technology can achieve competitive performance, then with its level of integration, it can pave the way for low-cost fully integrated THz imaging systems for large-volume applications spanning from defense to consumer and medical electronics.

It is easier to see these requirements in the context of a transmitter antenna, but the reasoning still applies to a receiving antenna due to reciprocity. We now discuss the design and implementation of a lens-less multipixel THz receiver with antenna and detector co-design on a 250 μm bulk silicon substrate with 10 Ω-cm resistivity.

Integrated 4×4 Pixel THZ Camera in SiGe BICMOS

We now describe the design, and implementation of a direct-detection-based 4×4 pixel THz camera in 0.13 μm SiGe BiCMOS process.

The chip is implemented in the IBM8hp process, which is a 0.13 μm SiGe BiCMOS process. The process provides 120 nm NPN bipolar transistors with peak $f_T/f_{max}$ of 200/285 GHz. This process has substrate resistivity of about 10 Ω-cm and five levels of copper metal layers, including M1, M2, M3 and M4 (each with a thickness of 0.32 μm), and M5 (with a thickness of 0.55 μm), as well as two levels of aluminum (with thicknesses of 1.25 μm and 4 157 μm).

Architecture, Integrated Antenna, Detector and Baseband

The choice of a front-end for an architecture which can be scaled to a large number of pixels is advantageous with respect to its sensitivity, scalability and power dissipation. Operating near and above $f_{max}$ of a technology, the incoming signal captured by the antenna cannot be amplified by a high-gain front-end LNA. It is advantageous to provide a circuit configured to reduce the Terahertz frequency of the impinging Terahertz radiation to a frequency amenable to processing in silicon circuitry. For the lowest noise performance, the Terahertz frequency signal can either be directly converted to DC through rectification or brought down to an intermediate frequency through harmonic mixing. While a down-converting architecture gives additional phase information and low noise performance due to optimum receiver architecture, it imposes stringent requirements such as routing of LO, maintaining phase coherence to all pixels, occupation of substantially large silicon area, and excessive power consumption. Sealing a down-converting architecture to a high-resolution imager with more than 100×100 pixels is therefore expected to be prohibitive in effort and in expense.

Figure 3:
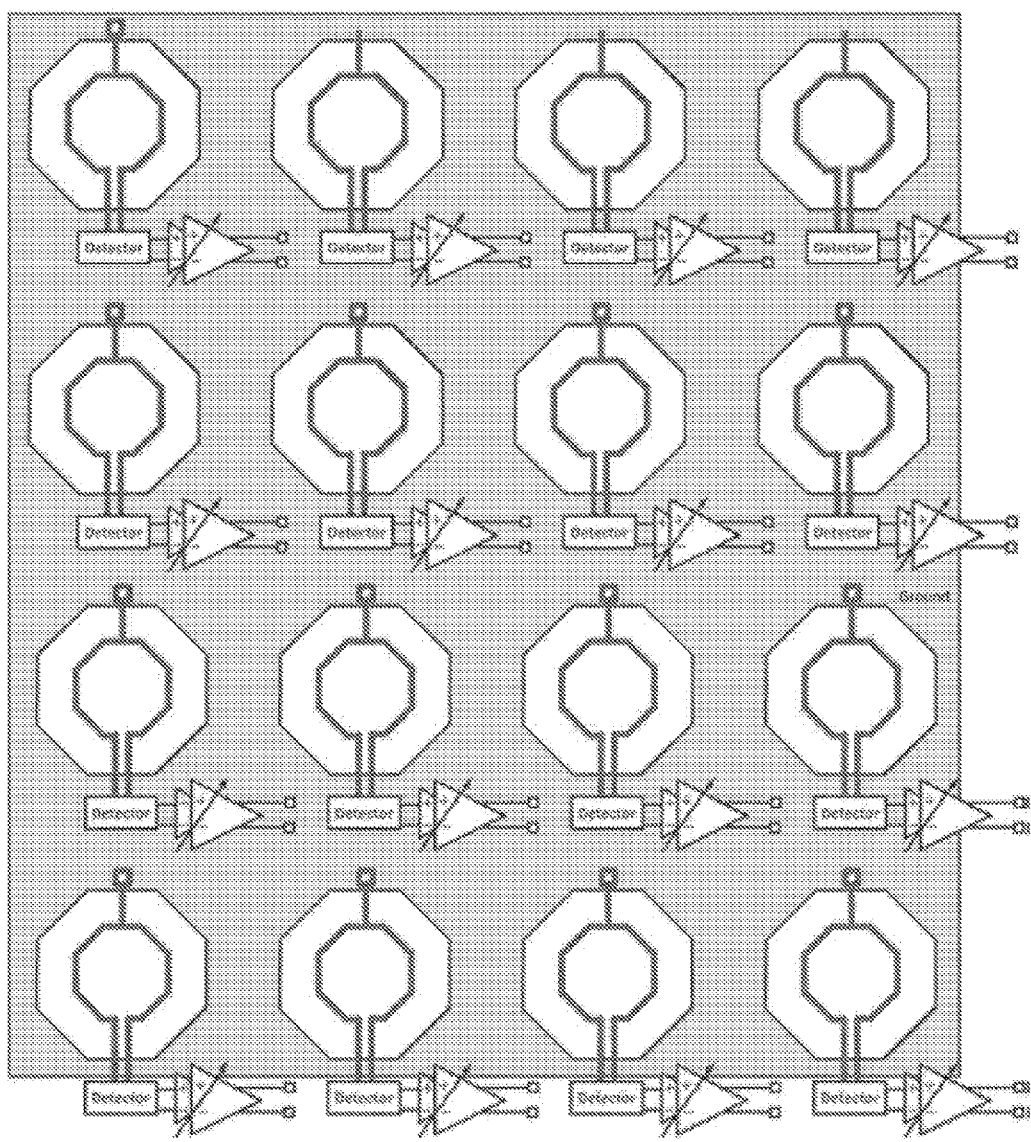
FIG. 3 is a schematic diagram showing the architecture of a 4×4 pixel imager chip.

We chose a direct detection scheme for the 16 pixel camera. The architecture is shown in FIG. 3. FIG. 3 is a schematic diagram showing the architecture of a 4×4 pixel imager chip. In one embodiment, 16 identical pixels are distributed across a 2.5 mm×2.5 mm size chip. Each pixel has an integrated antenna with a square law detector and an associate baseband with variable gain and adjustable bandwidth. The differential outputs of all the pixels come out to the pads, which provide terminals configured to provide an output signal for each pixel.

In the embodiment shown in FIG. 3, the pixel spacing is kept at 500 μm for antenna spacing of $\lambda_0/2$ at 300 GHz. The antenna comprises a near-full-wavelength loop, which has a property of reducing surface-wave power lost in TE modes. The chip was designed to have maximum sensitivity for radiation from the backside of the substrate.

The suppression of surface-waves and maximization of directivity in one direction relies on manipulation of currents. The design can be tailored to suit different materials with different dielectric constants. The conjugate matching between the onchip antenna and the front-end detector circuit (or front-end receiver circuit) can also be adjusted depending on the detection technology. The power loss to surface-waves can be minimized by adjusting the antenna loop diameter, the ground aperture and the antenna width. The antenna and detector co-design results in improved sensitivity.

As shown in FIG. 4A and FIG. 4B, for as ungrounded substrate, the paths length between the primary $A_{f1}$ and the different secondary sources ($A_{f2}, A_{f3}$, etc.) on the front side of the silicon die, after suffering multiple reflections, is the same as the primary source $A_{b1}$ and the different secondary sources ($A_{b2}, A_{b3}$, etc.) on the backside of the silicon die, after suffering multiple reflections, it can be shown that the efficiency of the antenna is maximized, when the sources ($A_{b1}, A_{b2}, A_{b3}$, etc.) on the backside add coherently in phase. This implies that total path length ($\sim 2h = \lambda_{s1}$). However, this also maximizes radiation from the front-side of the die due to phase coherence between $A_{f1}, A_{f2}, A_{f3}$, etc., implying the gain of the antenna is halved. FIG. 4A is a perspective diagram of a full-wavelength loop antenna on an ungrounded substrate. The full-wavelength loop antenna on an ungrounded substrate maximizes efficiency when front-side and back-side radiated power at the boresight are the same. FIG. 4B is a schematic cross-sectional diagram of the full-wavelength loop antenna on an ungrounded substrate.

Figure 5B:
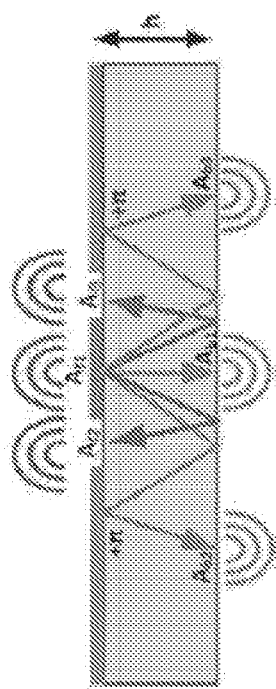
FIG. 5B is a schematic cross-sectional diagram of an oscillating current element on an ungrounded substrate.
Figure 5A:
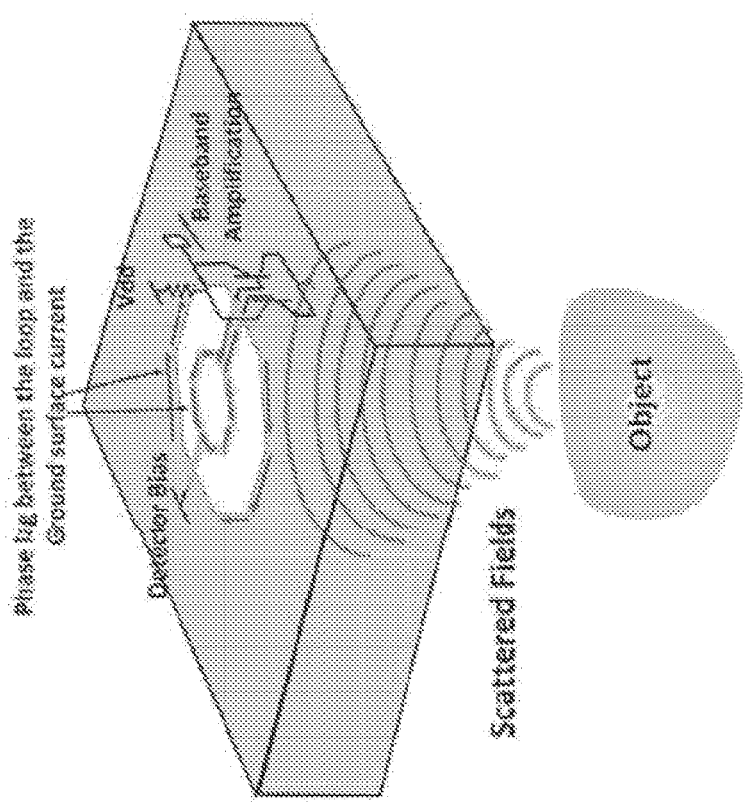
FIG. 5A is a perspective diagram of a full-wavelength loop antenna on a grounded substrate.

In order to block front-side radiation, a ground plane with an aperture opening is placed on metal 1, as shown is FIG. 5A. FIG. 5A is a perspective diagram of a full-wavelength loop antenna on a grounded substrate. A ground plane with an aperture suppresses front-side radiation and increases gain, and therefore responsivity, from backside radiation. FIG. 5B is a schematic cross-sectional diagram of the full-wavelength loop antenna on an ungrounded substrate.

The reflected waves at the ground plane, suffer an additional phase difference of π, as shown in FIG. 5B. Therefore for a substrate of $h \sim (2n-1)\lambda_{s1}/4$, $n \subset /+$, the secondary sources at the backside ($A_{b1}, A_{b2}, A_{b3}$, etc.) are in phase, while die front-side ($A_{f1}, A_{f2}, A_{f3}$, etc.) will be out-of-phase.

The radiation properties of the grounded and ungrounded loop antennas are shown in FIG. 6A through FIG. 6D.

FIG. 6A is a schematic diagram of a full-wavelength loop antenna without a ground plane and without an aperture opening.

FIG. 6B is a diagram that illustrates the three dimensional form of the radiated signal and also shows the Smith chart calculation of the radiation profile of the antenna of FIG. 6A.

The substrate height is optimized for efficiency, which implies h=150 μm in the absence of ground plane and h=220 μm in the presence of ground plane at an operating frequency of 300 GHz. As explained previously, for the ungrounded substrate, we see equal directivity in the front and backside lobes (12.5 dBi), while for the die with the ground plane, the front-side radiation is suppressed by almost 6 dBi compared to the back-side radiation (16.8 dBi). Due to the absence of the ground plane, the substrate mode configuration also changes. For the ungrounded substrate, the cut-off frequencies for both $TE_0$ and $TM_0$ modes are zero. It can be shown that for the substrate height of h=150 μm that maximizes efficiency, the only modes existing are the $TM_0$ and $TE_0$, each with wavelengths of 500 μm, of which $TM_0$ is the dominant mode. While, the $TE_0$ mode gets partially canceled due to the current configuration in a full-wavelength loop (though much lesser than the grounded case, since $2a \sim \lambda_{TE0}/4$ instead of $2a \sim \lambda_{TE0}/2$), the $TM_0$ mode of the different antennas in the array add in phase and come out from the side of the chip, which is demonstrated by the presence of strong sidelobes along the x direction in the x-y plane, as illustrated in FIG. 6B.

We can compare this with the case, where the loop has a ground plane with an aperture, as shown in FIG. 6C. FIG. 6C is a schematic diagram of a full-wavelength loop antenna with a ground plane and with an aperture opening.

In the embodiment shown in FIG. 6C, there are three modes existing, $TM_0$ ($\lambda_{TM0}$=309 μm), $TE_0$ ($\lambda_{TE0}$=346 μm) and $TM_1$ ($\lambda_{TM1}$=782 μm), of which $TM_1$ and $TE_0$ are the dominant modes. The $TE_0$ mode gets partially canceled with the fall-wavelength loop, and the spacing in the array corresponds to nearly $\lambda_{TM1}/2$ which, suppresses $TM_1$. The resultant pattern is much cleaner and sharper as is seen in FIG. 6D. FIG. 6D is a diagram that illustrates the three dimensional form of the radiated signal and also shows the Smith chart calculation of the radiation profile of the antenna of FIG. 6C.

Figures 7A, 7B, 7C, 7D:
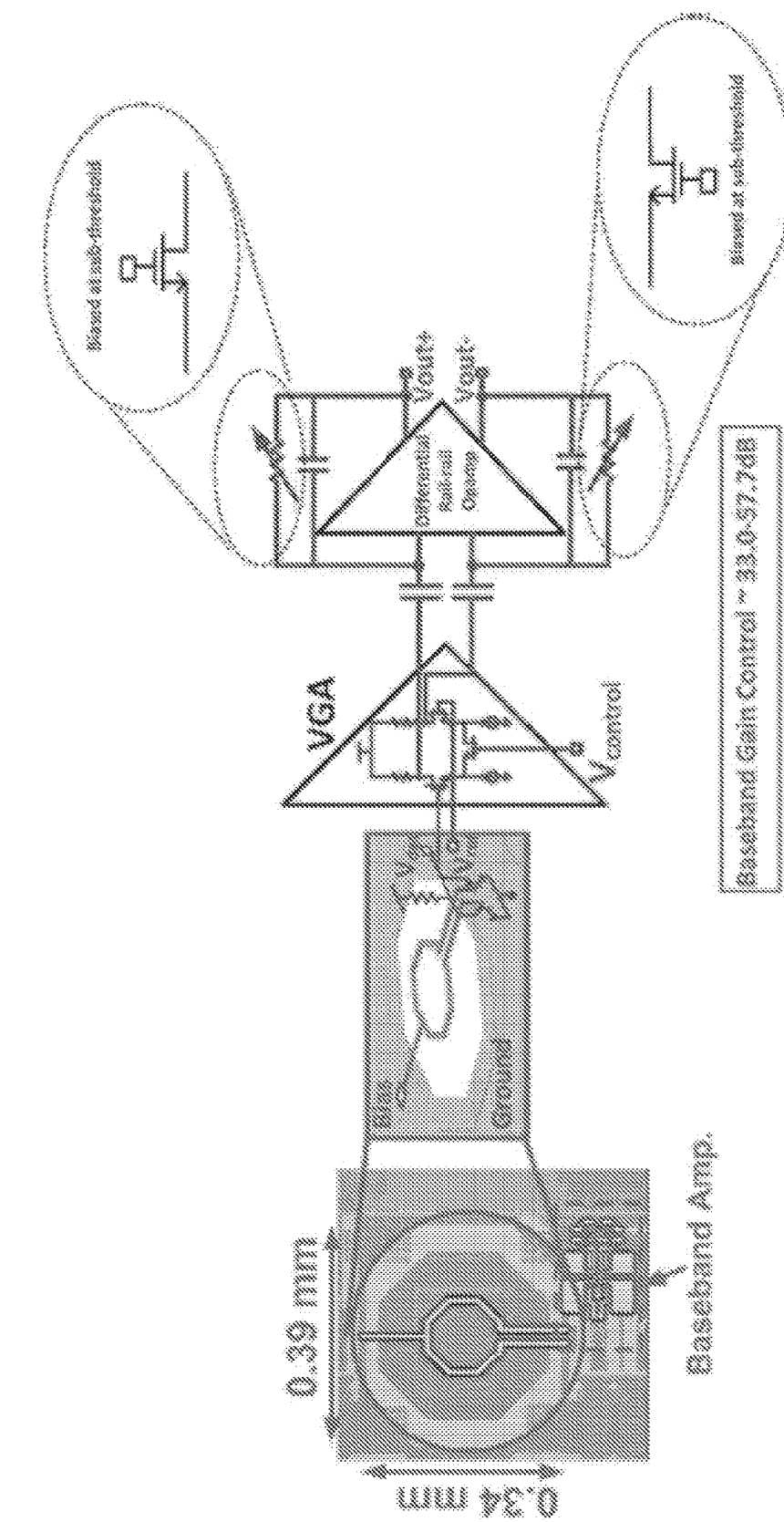
FIG. 7A is an image of a THz imaging receiver in silicon with on-chip antenna, front-end detector (or front-end receiver) and baseband amplification with 24.7 dB tuning range.
FIG. 7B, FIG. 7C and FIG. 7D are circuit diagrams that illustrate an embodiment of the THz imaging receiver of FIG. 7A.

FIG. 7A is an image of a THz imaging receiver in silicon with on-chip antenna, front-end detector and baseband amplification with 24.7 dB tuning range.

FIG. 7B, FIG. 7C and FIG. 7D are circuit diagrams that illustrate as embodiment of the THz imaging receiver of FIG. 7A.

The ground loop diameter is adjusted for maximizing the responsivity of the detector from backside radiation. The ground, aperture diameter results in a return current near the edge of the aperture, which is phase-lagged with respect to the radiation-induced current distribution on the loop. This can change the overall input impedance of the resonant antenna. A series inductance is provided by two extended arm lengths, 100 μm each, that allow near-conjugate, match with the differential input of the detector for maximum radiative power transfer. The entire array structure of 16 antennas with ground plane apertures in a lossy 2.5 mm×2.5 mm lossy silicon substrate, is simulated in HFSS, to capture the coupling of the finite thickness of the substrates. However, the differential input impedance of the antenna at the edges ($Z_{in}$=32+j59Ω) were almost same as the ones in the middle of the array $Z_{in}$=33.5+j58Ω.

The front-end detector is based on square-law detection, which converts the incoming THz radiation into a change in output DC voltage. The detector comprises a differential SiGe pair, where the load resistance is attached to the common mode point. The biasing and the load are optimized for lowest noise performance. A low-cost low-power THz imager advantageously should have high responsivity and low NEP without the need for additional custom, corrective measures. A simple analysis reveals that for 100 nW of THz power-captured by the effective antenna aperture on-chip a SNR greater than 30 dB can be achieved with a 10 ms integration, time if NEP is less than 10 pW/√Hz.

Figure 8B:
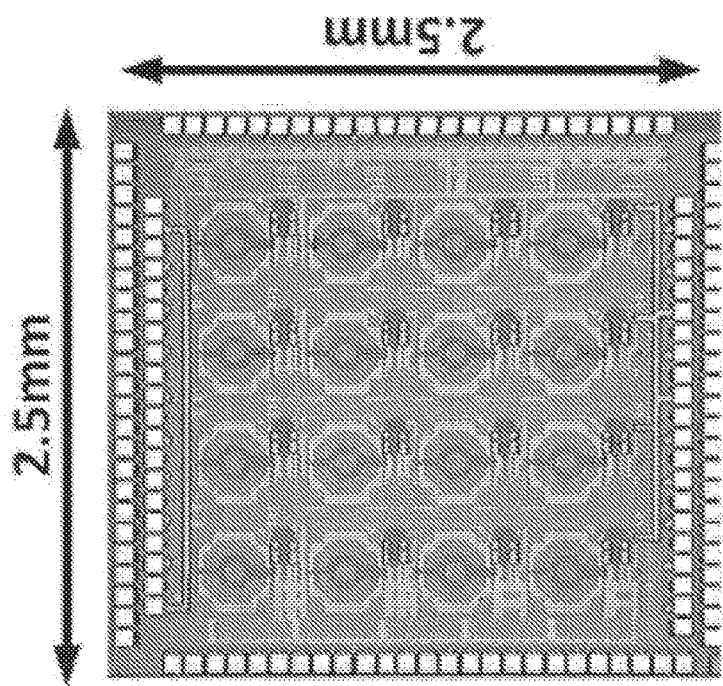
FIG. 8B is a die micrograph of the THz imager.
Figure 8A:
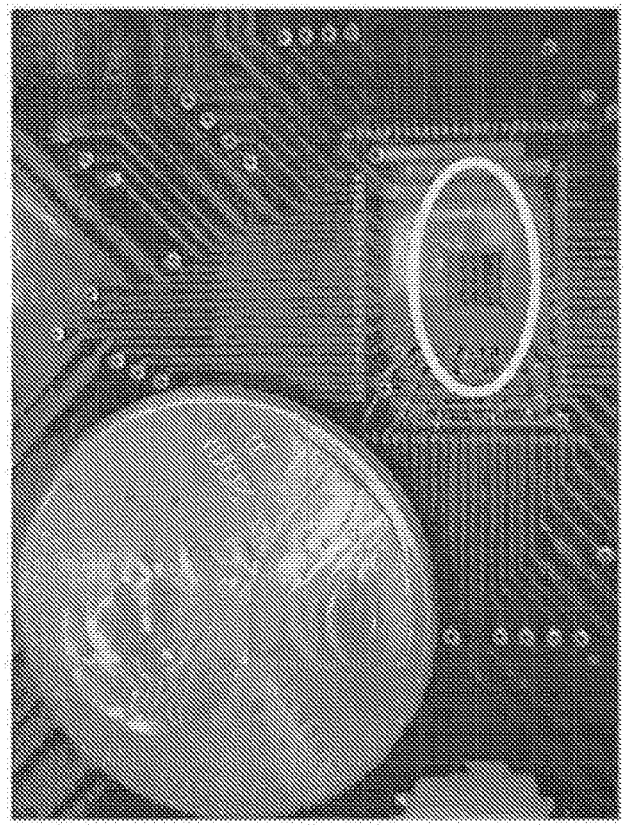
FIG. 8A is an image of the THz imager mounted on a PCB, with a US one cent piece showing the relative scale of the device.

FIG. 8A is an image of the THz imager mounted on a PCB, with a US one cent piece showing the relative scale of the device.

FIG. 8B is a die micrograph of the THz imager.

Measurement Results at Room Temperature

Figure 9B:
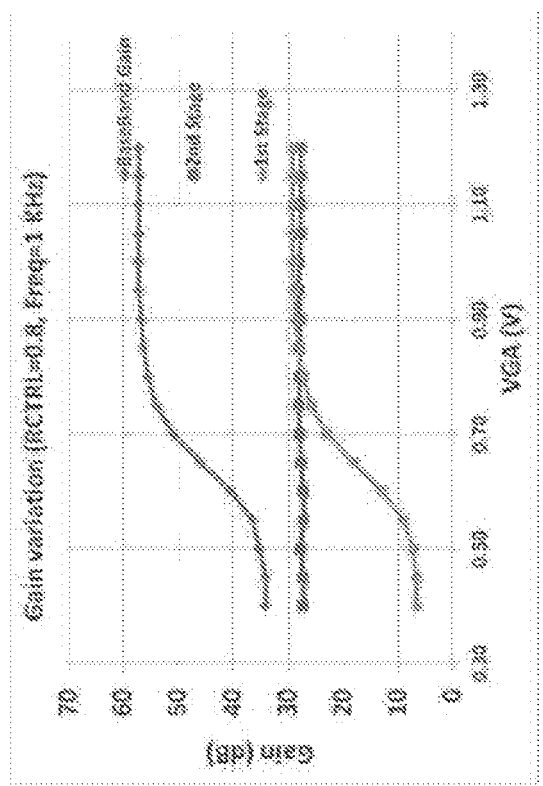
FIG. 9B is a graph that shows the gain variation with the VGA settings is also shown.
Figure 9A:
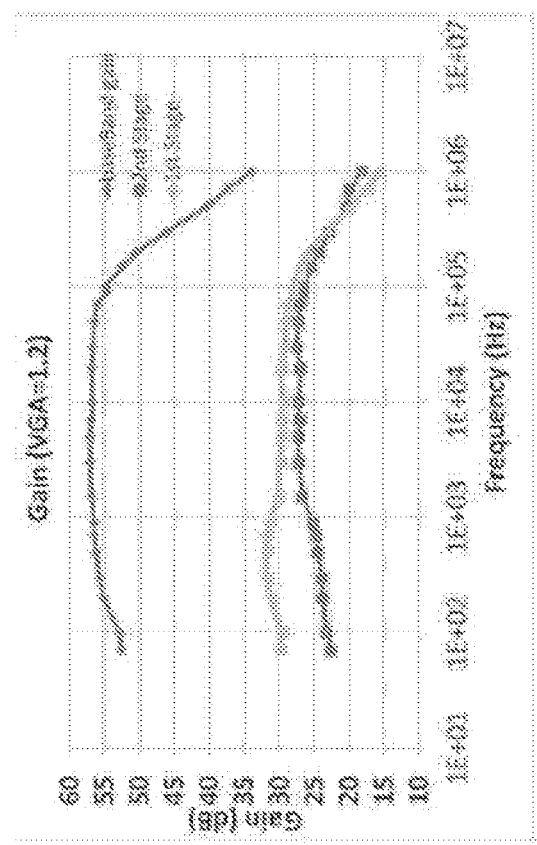
FIG. 9A is a graph that shows the frequency response of the baseband amplification showing a bandpass response which rejects DC offsets and low-frequency drifts.

The baseband is measured as a breakout structure. The results are shown in FIG. 9A and FIG. 9B. FIG. 9A is a graph that shows the frequency response of the baseband amplification showing a bandpass response which rejects DC offsets and low-frequency drifts. FIG. 9B is a graph that shows the gain variation with the VGA settings is also shown. The baseband has a peak voltage gain of 57.7 dB with a 3 dB bandwidth from 100 Hz to 100 KHz. The gain can be varied from 33-57.7 dB using the VGA control.

Figure 10:
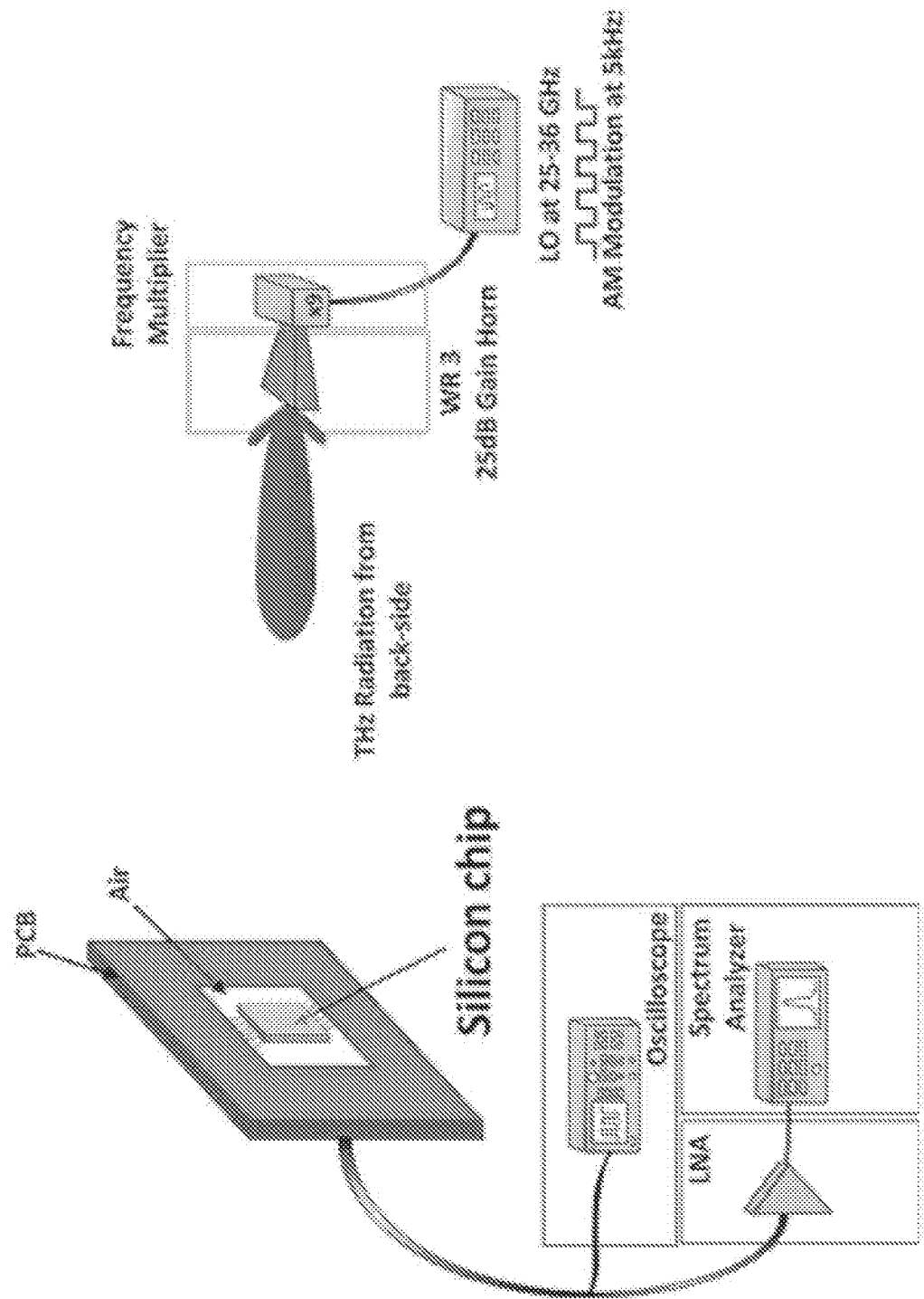
FIG. 10 shows a set-up for measuring responsivity and NEP of the imager.

The experimental set up for responsivity and NEP measurements is shows in FIG. 10. All measurements were done at room temperature. A custom WR-3 source, comprising a chain of multipliers available from Virginia Diodes, Inc., 979 Second Street, S.E. Suite 309, Charlottesville, Va. 22902-6172, is used as the THz source with a 25 dB Standard gain. WR-3 horn antenna. The radiation is captured by the chip from the backside of the substrate where it has the highest directivity. Responsivity is characterized in the far-field of a WR-3 source and the noise profile is measured using a spectrum analyzer, buffered by an external LNA. The THz radiation was chopped at a frequency of 5 KHz and the baseband output was observed in an oscilloscope. The entire setup was calibrated with an Erickson PM4 mm-submm wave power meter available from Virginia Diodes, Inc. Each pixel in the receiver was irradiated with measured 390 nW and 160 nW of power at 0.25 THz and 0.30 THz, respectively, at a far-field distance of 50 mm.

Figure 11:
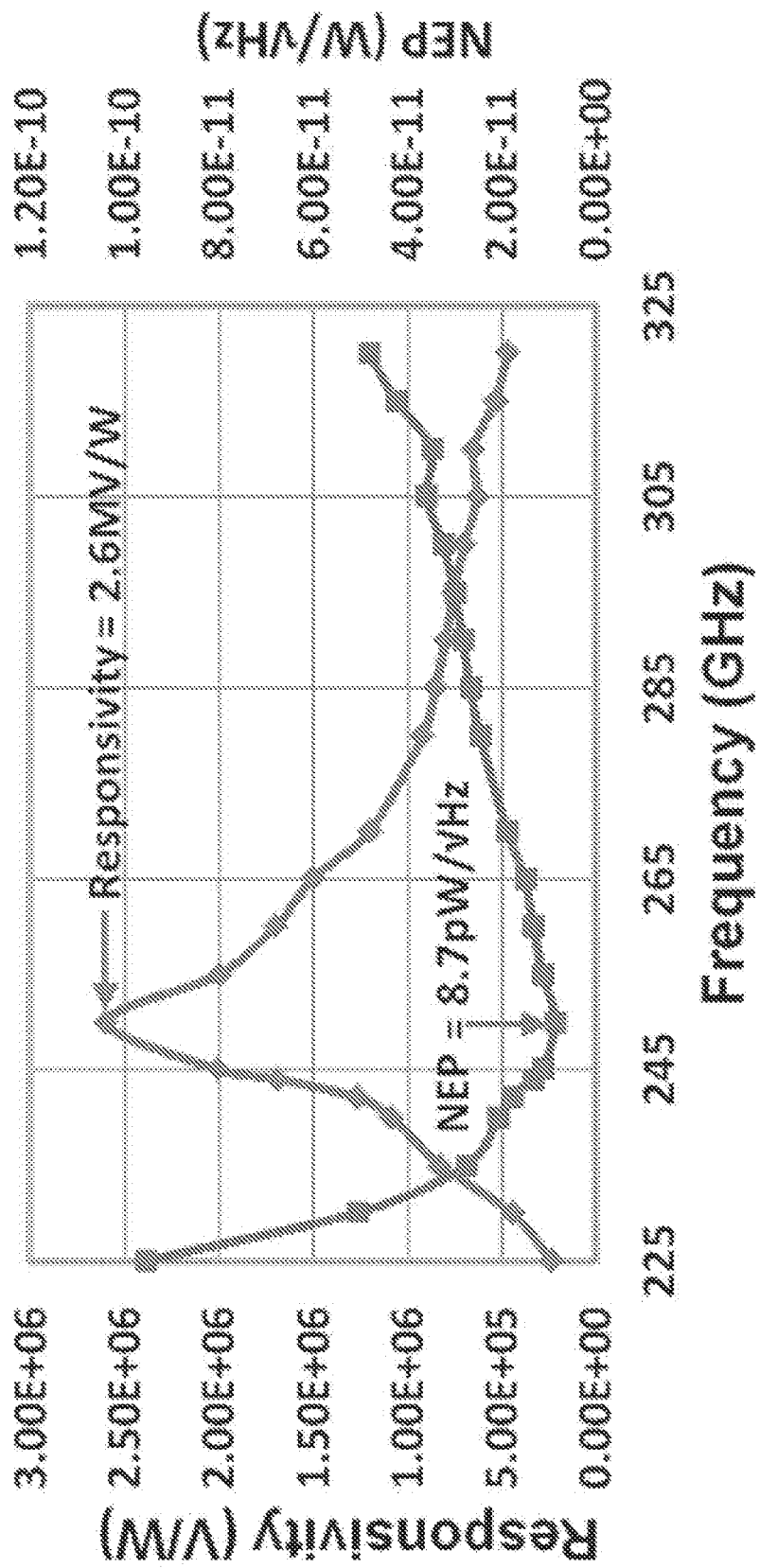
FIG. 11 is a graph that shows the measured responsivity and NEP of one pixel in the THz receiver.

The receiver achieves a peak responsivity of 2.6 MV/W and 700 kV/W, and a NEP of 8.7 pW/√Hz and 32.4 pW/√Hz at 0.25 THz and 0.3 THz, respectively. To the best of our knowledge, this is the lowest reported NEP in silicon at THz frequencies, without using expensive postprocessing or external silicon lens. Simulations predict that substrate thickness optimization through back-lapping can achieve a NEP of near 4 pW/√Hz, comparable to typical noise performance achieved in cooled microbolometers. The entire chip draws proximately 93 mW of power. Each detector draws less than 1 mW of quiescent DC power. FIG. 11 is a graph that shows the measured responsivity and NEP of one pixel in the THz receiver.

Figure 12B:
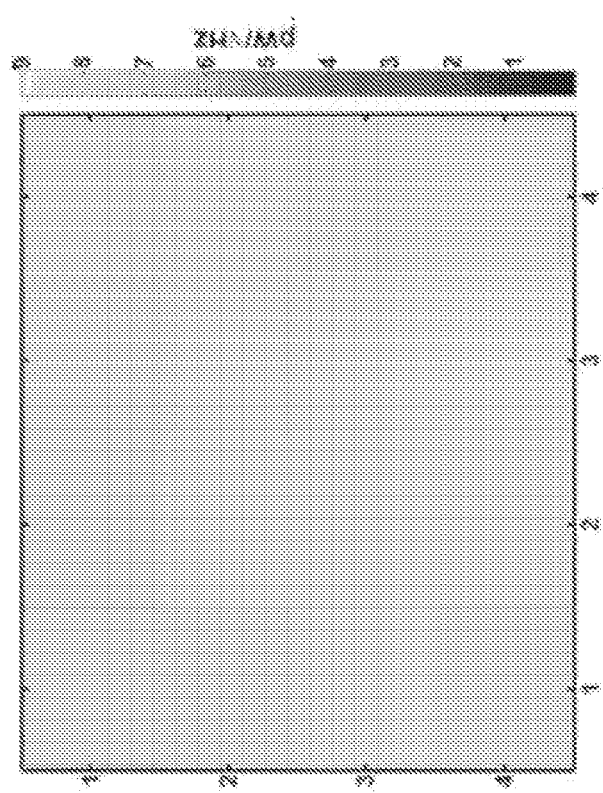
FIG. 12B is a graph that shows the results NEP measurements of 16 pixels at 0.25 THz showing sub-10 pW/√Hz for all pixels.
Figure 12A:
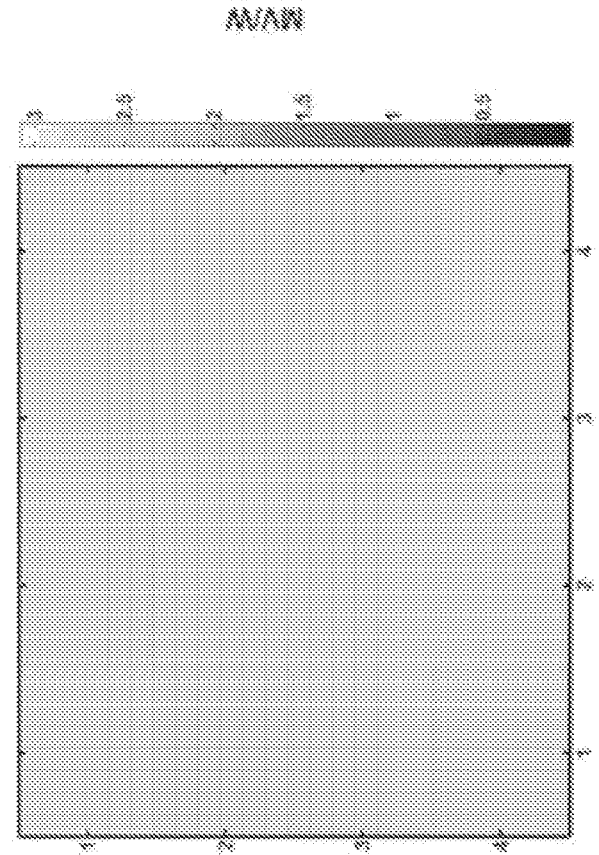
FIG. 12A is a graph that shows the results of responsivity measurements of 16 pixels at 0.25 THz.

The measured responsivities Rv of the 16 pixels across the chip, at 0.26 THz, for a chopping frequency of 5 KHz is shown in FIG. 12A and FIG. 12B. FIG. 12A is a graph that shows the results of responsivity measurements of 16 pixels at 0.25 THz. The image shows negligible variation across the 16 pixels of the chip. The responsivity variation across the chip occurs due to mismatches and also due to edge effects of the silicon die on the antenna response. FIG. 12B is a graph that shows the results NEP measurements of 16 pixels at 0.25 THz showing sub-10 pW/√Hz for all pixels. The measured minimum is 6.8 pW/√Hz. Responsivity of a single pixel peaks at a frequency of 0.26 THz of the incoming radiation. The results indicate almost 10× improvement in sensitivity over previous results near 0.3 THz in an un-thinned 250 μm bulk substrate with 11-16 Ω-cm. This corresponds to a 10× increase in acquisition speed at a modest power dissipation of 6 mW/pixel, which include baseband stages with variable gain from 33-57.7 dB, loading to higher SNR and better contrast in images, particularly important for biological specimens which have low-contrast variations.

FIG. 13A is a diagram showing a measurement setup for focusing emitted THz beam to a diffraction-limited spot size on the focal plane which is imaged by the THz receiver by raster-scanning. The radiation is again, captured from the backside of the silicon die and the output is measured by a locking amplifier synchronized with the chopping signal. The lenses identified as TPX lenses are constructed from Polymethylpentene (4-methyl-1-pentene). TPX is a trademark of Mistui chemicals. TPX is a hard, solid material, which can be mechanically shaped into various optical components such as lenses and windows. There are various sources of lenses made of TPX, including, for example, Zomega Terahertz Corporation, 15 Tech Valley Dr. Suite 102, Fast Grenbush, N.Y. 12061.

FIG. 13B is an image of the silicon THz imager mounted on a PCB. The PCB is connected to a motorized translational stage. The chip is raster scanned over the focal plane of 5 mm×5 mm, and the output voltage is plotted in a 2D plane.

Figures 14A, 14B, 14C:
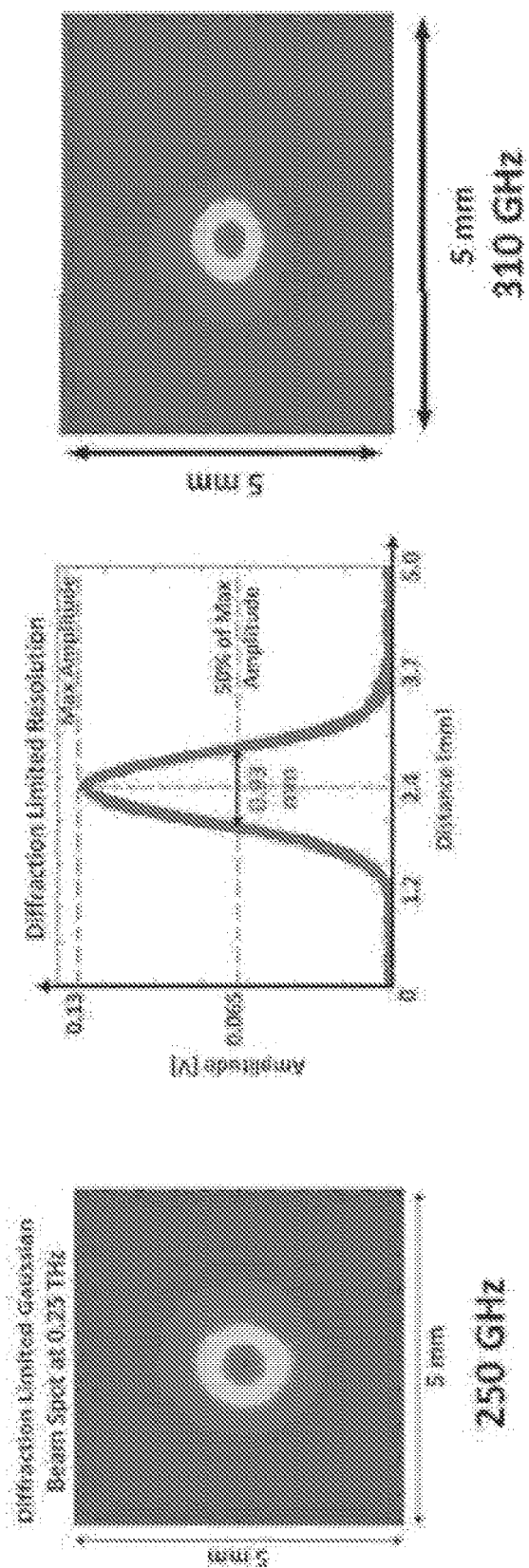
FIG. 14A is an image showing the measured spot size of the focused beam at 0.26 THz on the focal plane in transmission-mode setup at 260 GHz.
FIG. 14B is a graph of the measured and calculated diffraction profile.
FIG. 14C is an image showing the measured spot size of the focused beam at 0.31 THz on the focal plane in transmission-mode setup at 310 GHz.

FIG. 14A is an image showing the measured spot size of the focused beam, at 0.26 THz on the focal plane in transmission-mode setup at 260 GHz. FIG. 14B is a graph of the calculated and measured diffraction pre die on the focal plane. FIG. 14C is an image showing the measured spot size of the focused beam at 0.31 THz on the focal plane in transmission-mode setup at 310 GHz. The diffraction limited Gaussian focus spot for a 4-lens system at 0.26 THz follows closely the theoretical prediction. The full-width at half-maximum of the Gaussian beam is shown to be approximately 0.93 mm at 0.26 THz.

We have demonstrated the sensitivity of the detector by demonstrating capability of imaging, even when the signal power is spread, over a plane.

Figure 15B:
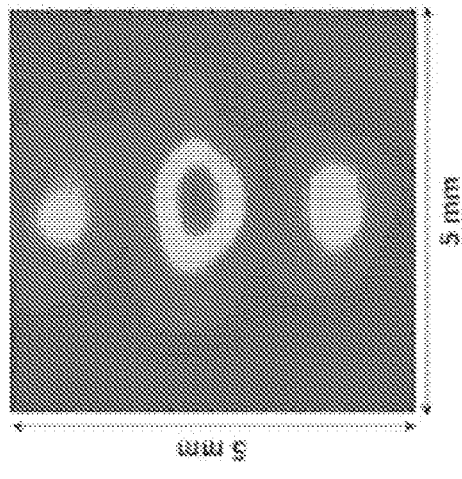
FIG. 15B is an image of the Fourier transform of the object on the focus plane of the lens at 0.26 THz.
Figure 15A:
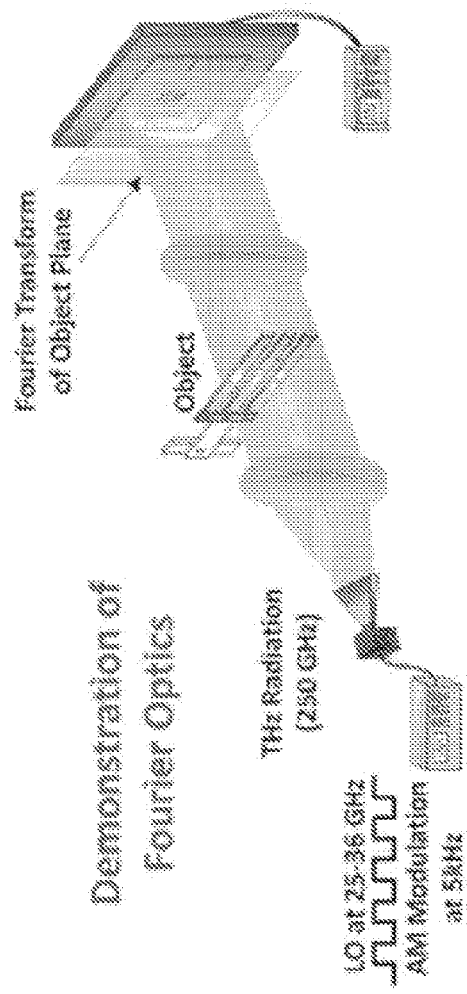
FIG. 15A is a schematic diagram of a setup used for the observation of an object, here a three pronged fork.

The sensitivity of the imager allows us to obtain a high-SNR image of the Fourier transform of the object (made of three metallic slits) even though the power is spread over the imaging plane and not confined to a spot. FIG. 15A is a schematic diagram, of a setup used for the observation of an object, here a three pronged fork. FIG. 15B is an Image of the Fourier transform of the object on the focus plane of the lens at 0.26 THz.

We now describe various demonstrations of imaging modalities and examples with the silicon-based chip. Transmission-mode and reflection-mode Imaging reveal different properties of the specimen, under investigation and offer different contrasting mechanisms.

Transmission-Mode Imaging

FIG. 16A is a diagram showing a measurement setup for making transmission-mode images in perspective view. A THz source with output power of 0.8 mW at 0.26 THz has been used. A focused THz spot is irradiated on the object, which is scanned on the focal plane. The transmitted radiation is again captured from, the backside of the silicon die and the output m measured by a locking amplifier synchronized with the chopping signal. The setup is aligned with a diode laser. FIG. 16B is an image of the silicon THz imager mounted on a PCB. FIG. 16C and FIG. 16D are images of parts of the measurement setup for making, transmission mode images. FIG. 16E is a diagram showing a measurement setup for making transmission-mode images in side view.

Results of Transmission Mode Imaging

FIG. 17A through FIG. 20B show imaging results with various specimens under the transmission modes of imaging.

Figure 17B:
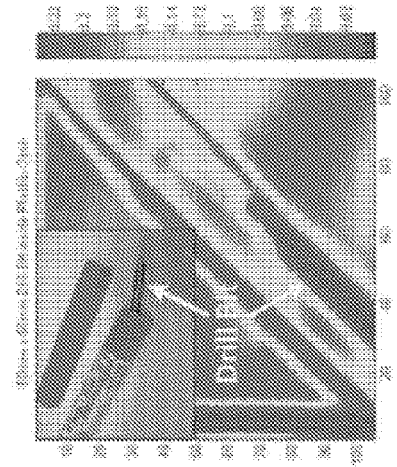
FIG. 17B is a transmission image of a drill bit is a plastic case.
Figure 17D:
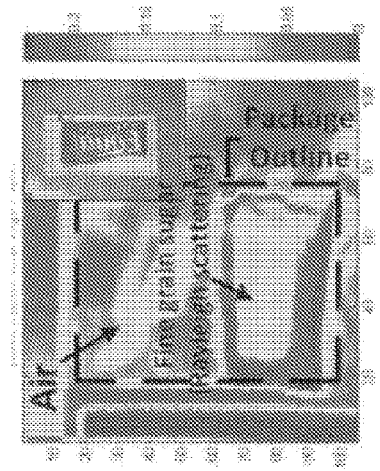
FIG. 17D is a transmission image of fine grain sugar in a paper packet.
Figure 17A:
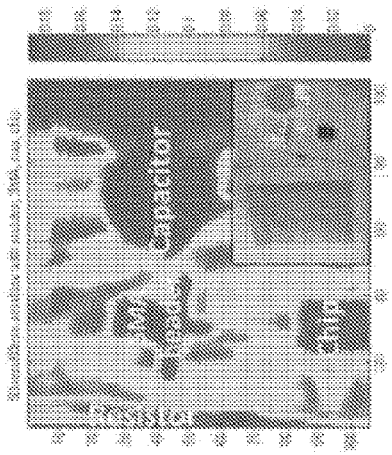
FIG. 17A is a transmission image of a resistor, a capacitor, an SMA header and a chip that were imaged trough a paper envelope.
Figure 17C:
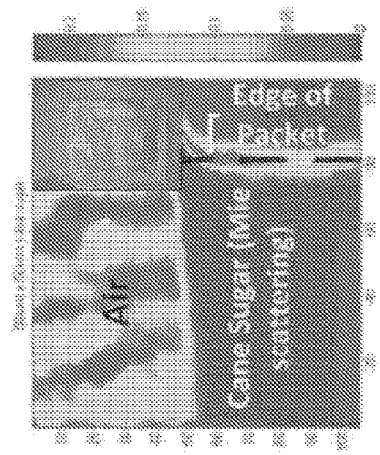
FIG. 17C is a transmission image of cane sugar in a paper packet.

THz waves can penetrate through plastic, paper and packaging materials. FIG. 17A is a transmission image of a resistor, a capacitor, an SMA header and a chip that were imaged trough a paper envelope. The inset shows the envelope and visual images of the electronic components. FIG. 17B is a transmission image of a drill bit in a plastic case. The inset shows the drill bit and the plastic case. FIG. 17C is a transmission image of cane sugar in a paper packet. The inset shows the paper packet. FIG. 17D is a transmission image of fine grain sugar in a paper packet. The inset shows the paper packet. The transmission line imaging examples show the penetrative property of THz through paper, plastic and demonstrating difference of interaction with scatterers of various sizes compared to the wavelength (sugar packets with fine and coarse grained sugar).

FIG. 18A is an optical image and FIG. 18B is a THz transmission line image of a key. The image of the key inside the opaque envelope (inside can be only seen by holding against strong light) shows resolution nearing 1 mm.

FIG. 18C is an optical image of a conference ID badge, and FIG. 18D is a THz transmission line image of the RFID chip and the loop antenna inside the conference ID badge. These transmission line images show near-1-mm resolution.

THz radiation is very sensitive to water absorption. This is a significant feature which can be exploited in the contrast of healthy tissues against tumorous sites, where differences in water content and tissue density are purported to be contrast agents.

FIG. 19A is an optical image and FIG. 19B is a THz transmission image of a dry leaf. FIG. 19C is an optical image and FIG. 19D is a THz transmission image of a green (water-containing) leaf. The differences between the transmission images are believed to be caused by the absorption of the THz signals by water.

FIG. 20A is an optical image and FIG. 20B is a transmission image of chicken tissue. The difference in transmission between adipose tissue and muscle tissue is evident in the images of a sample of chicken tissue observed at 0.26 THz.

Results of Imaging Using Reflective Geometry

THz imaging is also expected to be a promising tool in noninvasive diagnostics, as different materials have different dielectric, absorptive and reflective properties. While in transmission mode imaging, only the transmitted power is captured, while reflected and absorbed power is lost. On the other hand, in a reflection-based imaging setting, only reflective power is captured while transmitted and absorbed power is lost.

Figure 21B:
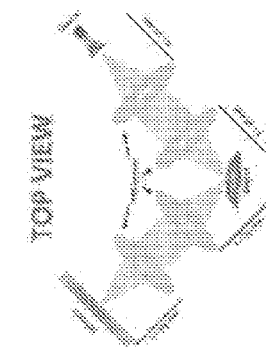
FIG. 21B is a top view schematic diagram of a THz reflection-mode imaging set-up.
Figure 21A:
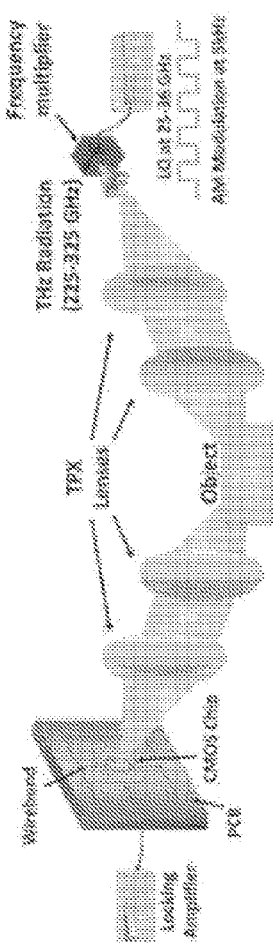
FIG. 21A is a perspective schematic diagram of a THz reflection-mode imaging set-up.
Figure 21C:
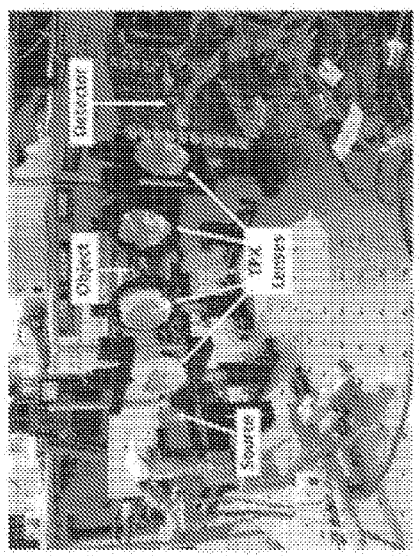
FIG. 21C is an image a THz reflection-mode imaging set-up.

FIG. 21A is a perspective schematic diagram of a THz reflection-mode imaging set-up. FIG. 21B is a top view schematic diagram of a THz reflection-mode imaging set-up. FIG. 21C is an image a THz reflection-mode imaging set-up.

FIG. 22A is an image showing the measured spot size of the focused beam at 0.26 THz on the focal plane in reflection-mode setup. FIG. 22B is an optical image of a metal screen having holes of 4 mm, diameter and FIG. 22C is a reflection mode THz image of the screen. FIG. 22D is an optical image of a metal key and FIG. 22E is a reflection mode THz image of the screen. The key is 44.2 mm long, and the dimensions given by bars 2210, 2220 and 2230 are 11.7 mm, 3.5 mm, and 18.8 mm, respectively.

Figure 23B:
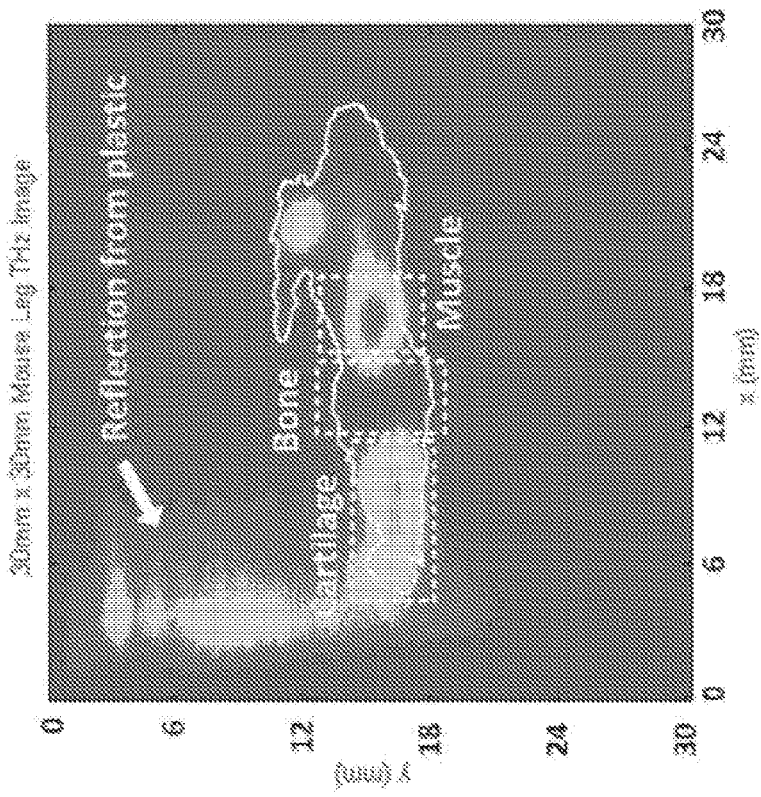
FIG. 23B is a THz reflection image showing bone, cartilage and muscle in the mouse leg.
Figure 23A:
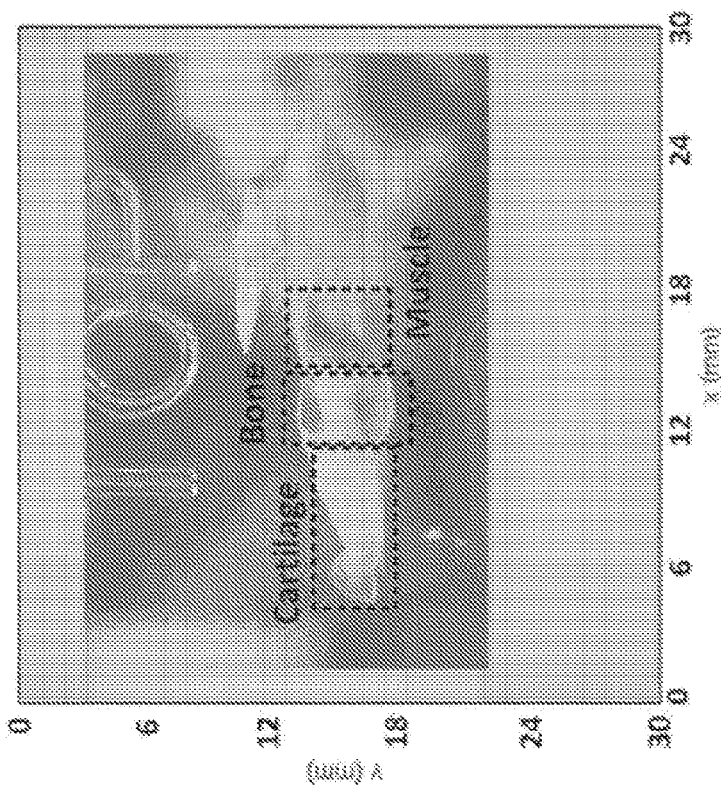
FIG. 23A is an optical image showing bone, cartilage and muscle in a mouse leg, which is fixed on a glass slide.

Contrast in a biological specimen in reflection-mode imaging is demonstrated in FIG. 23A through FIG. 23A is an optical image showing bone, cartilage and muscle in a mouse leg, which is fixed on a glass slide. FIG. 23B is a THz reflection image showing bone, cartilage and muscle in the mouse leg. A reflection from a piece of plastic is also seen. These images demonstrate the feasibility of noninvasive imaging at THz frequencies. The contrast between bones, muscles and cartilages is believed to be due to the differences in the dielectric properties of the different tissues.

Figure 27A:
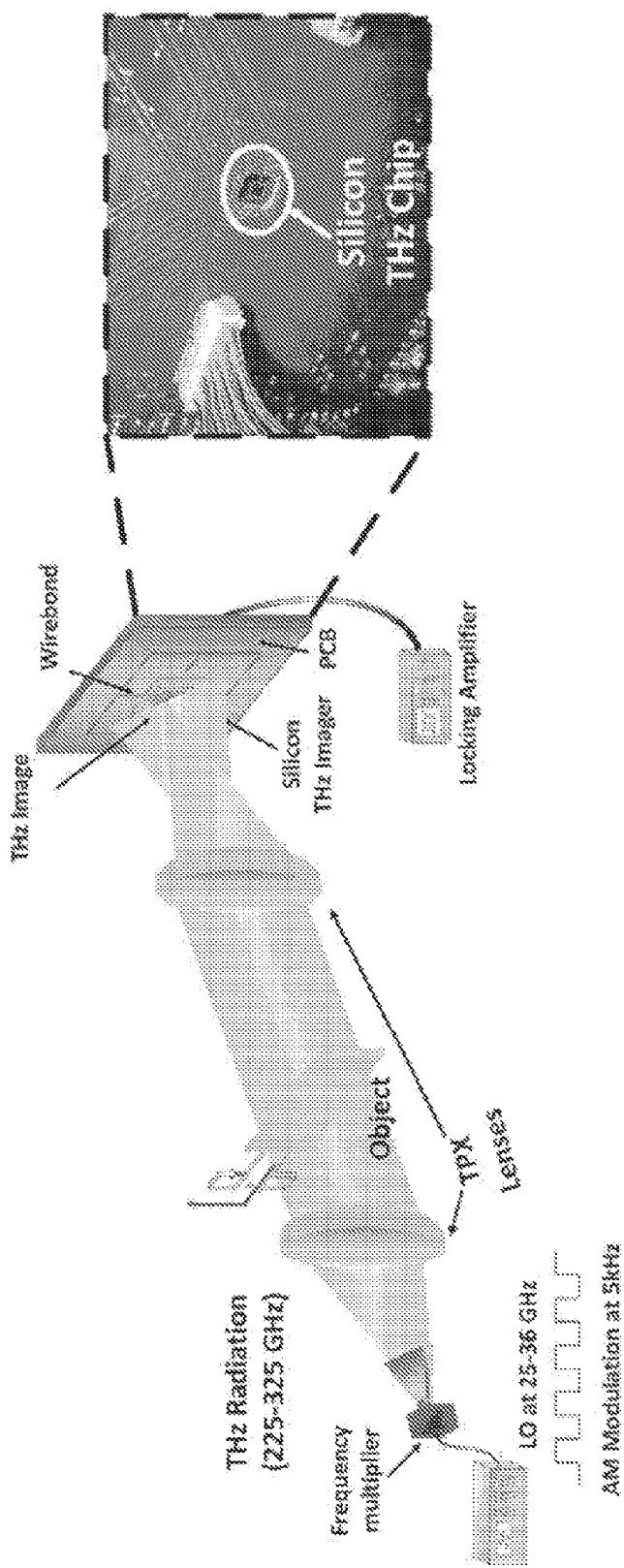
FIG. 27A is a perspective schematic diagram of a transmission imaging set-up where a part or all of the object is illuminated and an image is cast on the other side of the lens.

FIG. 27A is a perspective schematic diagram of a transmission imaging set-up where a part or all of the object is illuminated and an image is cast on the other side of the lens.

Figure 27B:
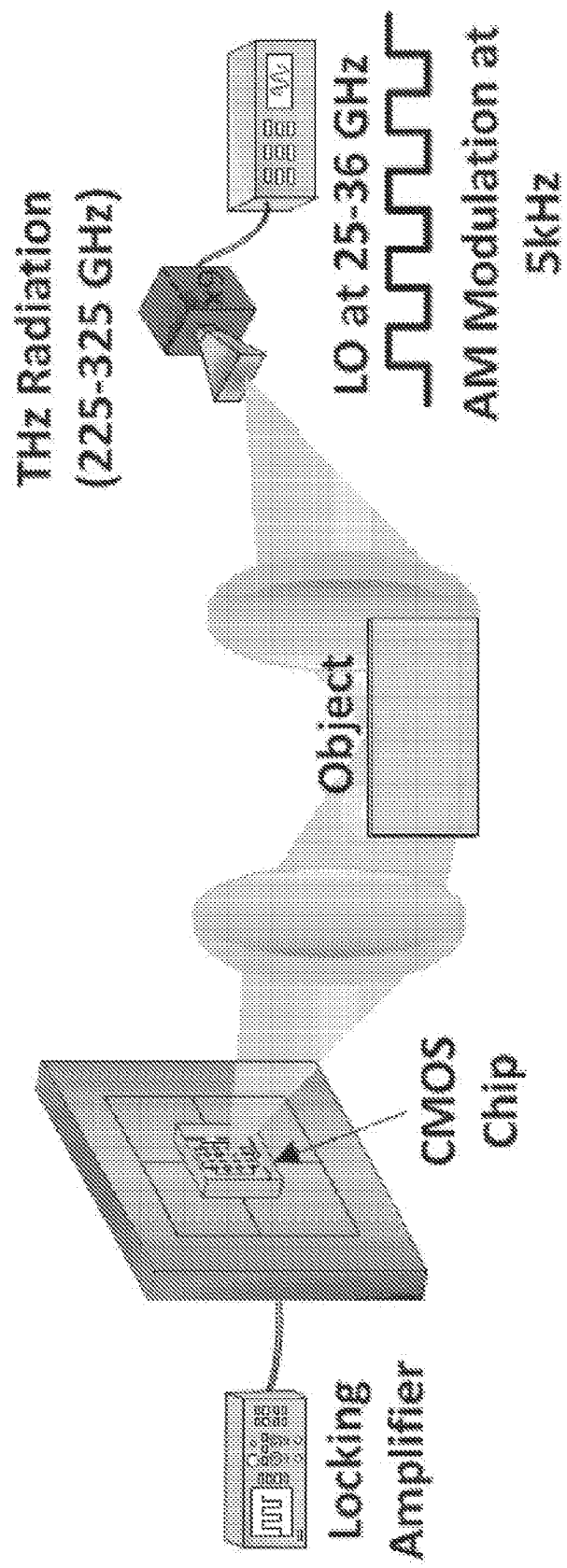
FIG. 27B is a perspective schematic diagram of a reflection imaging set-up where a part or all of the object is illuminated and an image is cast on the other side of the lens.

FIG. 27B is a perspective schematic diagram of a reflection imaging set-up where a part or all of the object is illuminated and an image is cast on the other side of the lens. The imaging arrangements of FIG. 27A and of FIG. 27B avoid the use of a focused beam which is raster-scanned on the object.

All-Silicon THz Imaging System

The previous examples showed the use of a silicon-based THz detector array chip and a custom THz source. We replaced the source with a CMOS chip having a 2×2 array of free-running, mutually injection locked Distributed Active Radiators near 0.29 THz, such as described in U.S. Ser. No. 13/282,193. This system constitutes a fully integrated silicon-based THz imaging system. FIG. 24A is a perspective schematic diagram of an all-silicon-based THz imaging setup with a 16-pixel BiCMOS detector array and 2×2 array of locked CMOS DARs near 0.29 THz. FIG. 24B is an image of the detector mounted on a PCB. FIG. 24C is an image of the 2×2 array transmitter chip, which measures 800 µm on a side. The CMOS chip free-running frequency is near 0.29 THz and the radiation is chopped at a frequency of 5 KHz by modulating the supply voltage.

Figure 25C:
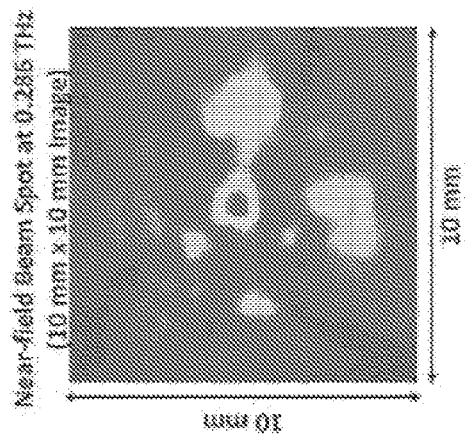
FIG. 25C is an image showing the near-field profile, obtained by scanning the detector array chip, when the two PCBs with the silicon chips are brought into each other's near-fields
Figure 25B:
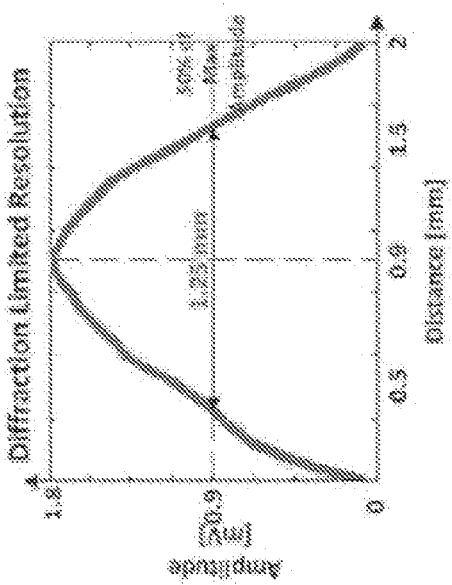
FIG. 25B is a graph of the calculated amplitude vs. distance.
Figure 25A:
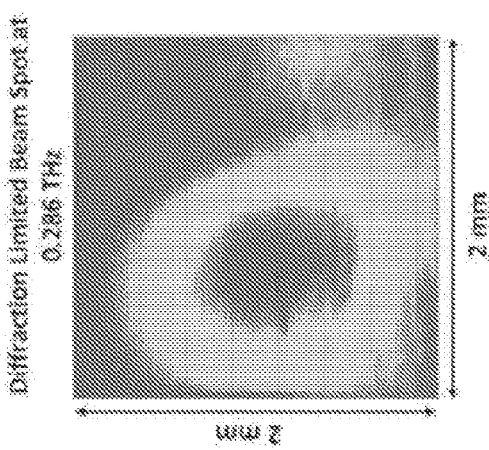
FIG. 25A is an image showing the diffraction-limited spot radiated by the CMOS source and imaged by the silicon detector array.

FIG. 25A is an image showing the diffraction-limited spot radiated by the CMOS source and imaged by the silicon detector array. The spot size is near 1 mm diameter. FIG. 25B is a graph of the calculated amplitude vs. distance. FIG. 25C is an image showing the near-field profile, obtained by scanning the detector array chip, when the two PCBs with the silicon chips are brought into each other's near-fields. Broadside spot and side-resonance fields due to the parallel plate waveguide effect can be seen in the field profile.

Figure 26B:
FIG. 26B is the metal object as seen is the first THz imaging demonstration with a CMOS source.
Figure 26A:
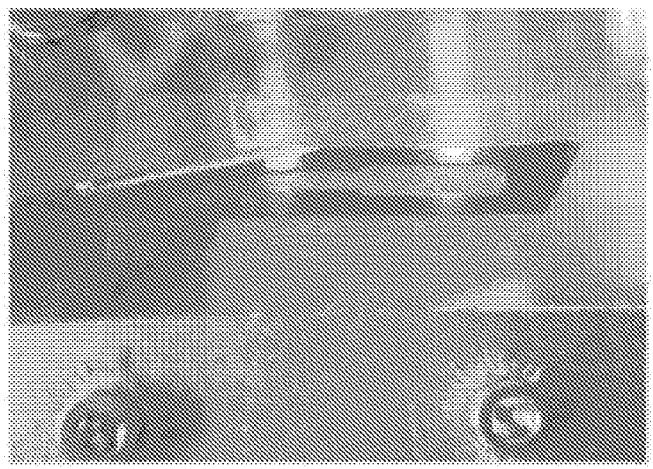
FIG. 26A is an optical image of a metal object having an aperture fixed on a glass support with two-sided tape.

We also demonstrate the first ever THz imaging demonstrated with a CMOS source at room temperature with no use of compound semiconductors or optics-based active devices far either signal generation or detection. This demonstration is shown in FIG. 26A and FIG. 26B. FIG. 26A is an optical image of a metal object having an aperture feed on a glass support with two-sided tape. FIG. 26B is the metal object as seen in the first THz imaging demonstration with a CMOS source.

Figure 28:
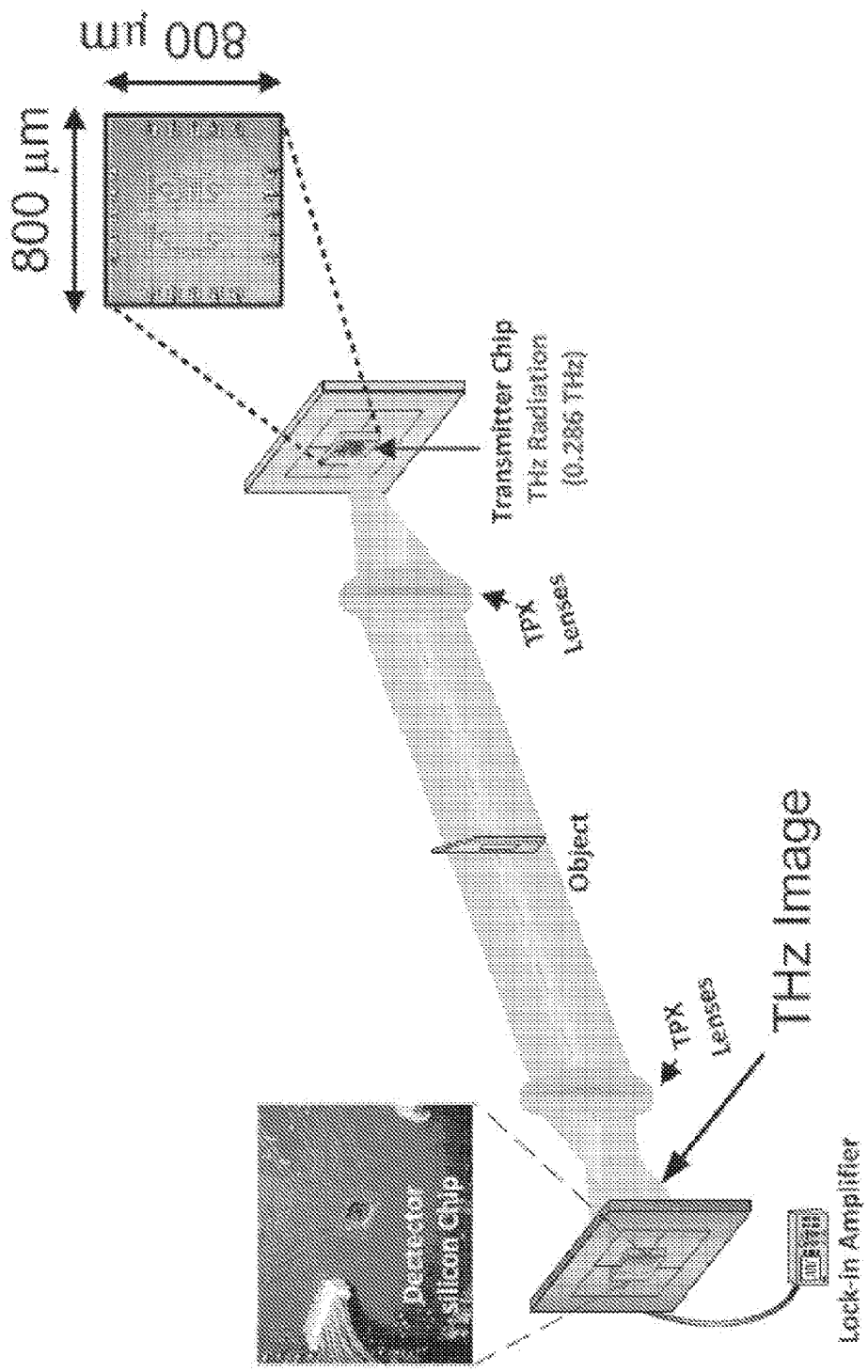
FIG. 28 is a perspective schematic diagram, of a transmission imaging set-up some or all of the object to be imaged is illuminated and an image is cast on the imager plane.

FIG. 28 is a perspective schematic diagram of a transmission imaging set-up some or all of the object to be imaged is illuminated and an image is cast on the imager plane.

Figure 29:
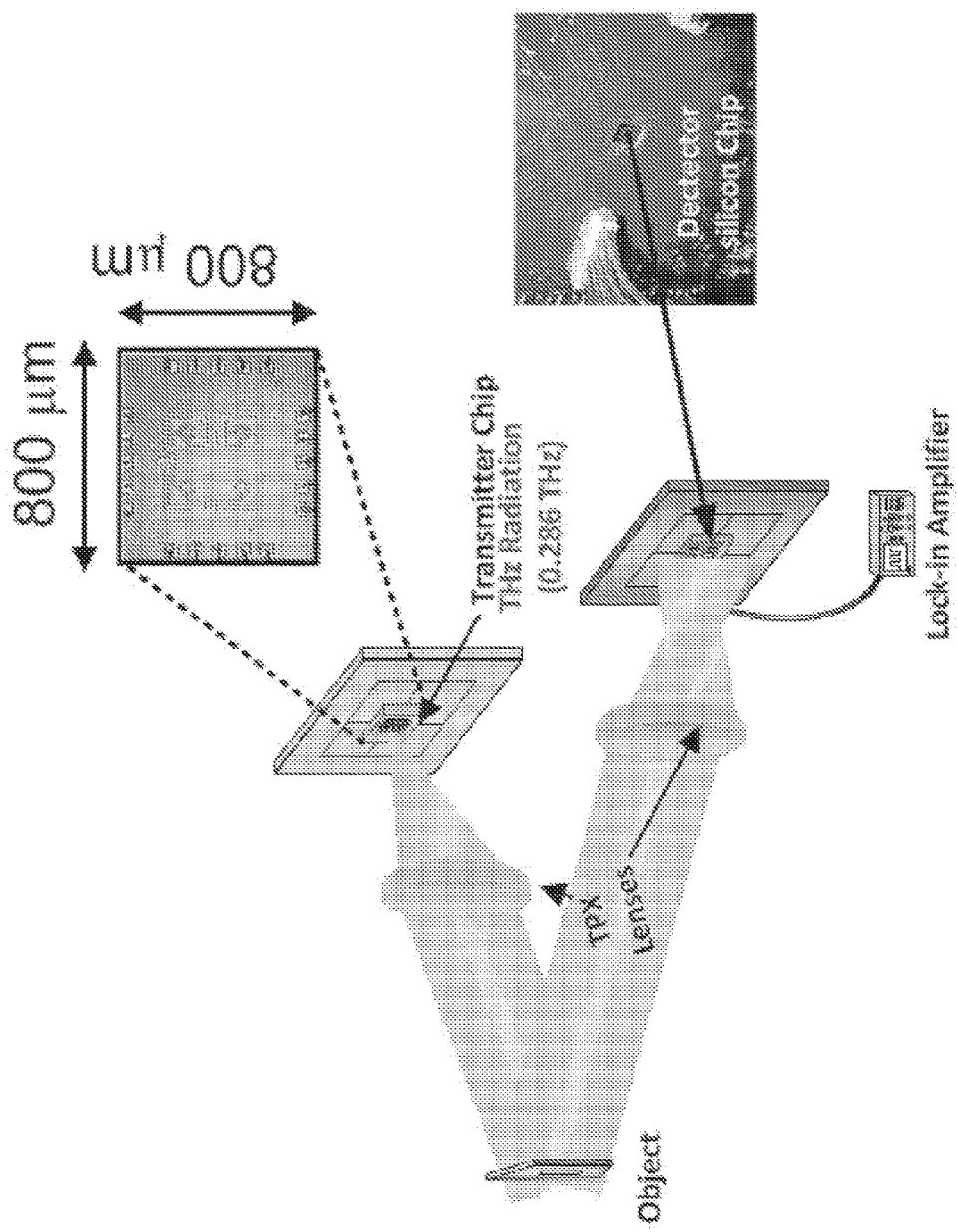
FIG. 29 is a perspective schematic diagram of a reflection imaging set-up some or all of the object to be imaged is illuminated and an image is cast on the imager plane.

FIG. 29 is a perspective schematic diagram of a reflection imaging set-up some or all of the object to be imaged is illuminated and an image is cast on the imager plane. The arrangements of FIG. 28 and FIG. 29 avoid the use of a focused beam and the necessity to raster scan the object or the image across the imager surface.

It is contemplated that any of the embodiments described herein can be controlled by a general purpose programmable computer operating under the control of one or more instructions recorded on a machine readable memory. For example, a microcomputer could control the relative motion of an object to be imaged and elements of the imaging system.

DEFINITIONS

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks CD-R disks (i.e. write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available is the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest, "Writing output data" or "writing art image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than, one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such, as a wired communication device or a wireless communication device, an output device such as a display terminal, and an input device such as a keyboard. The display terminal can be a touch screen display, in which case it can function as both, a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within, the microprocessor, which results are then commonly stored in cache memory for later use, so that the result can be displayed, recorded to a non-volatile memory, or used in further data processing or analysis.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified, response is generated, at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein, is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material, and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. An integrated circuit comprising a plurality of pixels, each of the plurality of pixels comprising:
    an antenna adapted to receive an incoming electromagnetic wave;
    circuitry adapted to downconvert a frequency of the received electromagnetic wave and generate an electrical signal in response; and
    a plurality of output terminals adapted to supply the electrical signals.

2. The integrated circuit claim 1 wherein each pixel of said plurality of pixels further comprises an amplifier.

3. The integrated circuit claim 2 wherein the amplifier disposed in each of the plurality of pixels has a variable gain and a variable frequency response.

4. The integrated circuit claim 1 wherein the frequency of the incoming electromagnetic wave is in the Terahertz range.

5. The integrated circuit claim 4 wherein the circuitry disposed in each of the plurality of pixels is adapted to downconvert the Terahertz frequency of the received electromagnetic wave to an intermediate frequency.

6. The integrated circuit claim 1 wherein the circuitry disposed in each of the plurality of pixels is further adapted to convert the incoming electromagnetic wave to a DC voltage.

7. The integrated circuit of claim 1 wherein the antenna disposed in at least one of the plurality of pixels is a full-wavelength loop antenna.

8. The integrated circuit of claim 7 further comprising a ground plane around the loop antenna.

9. The integrated circuit of claim 1 wherein said integrated circuit is configured to receive the electromagnetic wave from a backside of a substrate in which the integrated circuit is formed.

10. The integrated circuit of claim 1 wherein said substrate is a silicon substrate.

11. An imaging system comprising:
    an integrated circuit comprising a plurality of pixels, each of the plurality of pixels comprising:
    an antenna adapted to receive an incoming electromagnetic wave;
    circuitry adapted to downconvert a frequency of the received electromagnetic wave to generate an electrical signal in response; and
    a plurality of output terminals adapted to supply the electrical signals; and
    a source generating the electromagnetic wave.

* * * * *